(12) United States Patent
Penninger et al.

(10) Patent No.: US 10,143,747 B2
(45) Date of Patent: Dec. 4, 2018

(54) BREAST CANCER THERAPEUTICS

(75) Inventors: Josef Penninger, Vienna (AT); Daniel Schramek, Vienna (AT)

(73) Assignee: IMBA—INSTITUT FÜR MOLEKULARE BIOTECHNOLOGIE GMBH, Vienna (AT)

( * ) Notice: Subject to any disclaimer, the term of this patent is extended or adjusted under 35 U.S.C. 154(b) by 80 days.

(21) Appl. No.: 13/825,655

(22) PCT Filed: Sep. 22, 2011

(86) PCT No.: PCT/EP2011/066511
§ 371 (c)(1),
(2), (4) Date: Mar. 22, 2013

(87) PCT Pub. No.: WO2012/038504
PCT Pub. Date: Mar. 29, 2012

(65) Prior Publication Data
US 2013/0216550 A1 Aug. 22, 2013

(30) Foreign Application Priority Data

Sep. 22, 2010 (EP) .................................... 10178346

(51) Int. Cl.
| | | |
|---|---|---|
| *A61K 39/395* | (2006.01) | |
| *A61K 31/57* | (2006.01) | |
| *A61K 38/18* | (2006.01) | |
| *A61K 31/565* | (2006.01) | |
| *A61K 31/713* | (2006.01) | |
| *A61K 39/00* | (2006.01) | |

(52) U.S. Cl.
CPC ........ *A61K 39/3955* (2013.01); *A61K 31/565* (2013.01); *A61K 31/57* (2013.01); *A61K 31/713* (2013.01); *A61K 2039/505* (2013.01)

(58) Field of Classification Search
None
See application file for complete search history.

(56) References Cited

U.S. PATENT DOCUMENTS

2003/0021785 A1* 1/2003 Dougall ............ 424/146.1
2008/0107597 A1* 5/2008 Boyle .................. 424/1.49

FOREIGN PATENT DOCUMENTS

| JP | 2005-515159 | 5/2005 |
| WO | 99/53942 A1 | 10/1999 |
| WO | 0043553 | 7/2000 |
| WO | 02/098362 A2 | 12/2002 |
| WO | 2005060627 | 7/2005 |

OTHER PUBLICATIONS

Roudier et al (Clinical and Experimental Metastasis, 2006, 23:167-176).*
Elenbaas et al. (Genes & Development, 2001, 15:50-65).*
Banstetter et al. (Cancer Research, 2009, 69:4167; abstract from CTRC-AACR San Antonio Breast Cancer Symposium).*
Sordillo et al. (Cancer Supplement, 2003, 97:802-812).*
Collaborative Group (Lancet, 1997, 350:1047-1059).*
Ellis et al. (Journal of Clinical Oncology, 2008, 26:4875-4882).*
Cummings et al. (The New England Journal of Medicine, 2009, 361:756-765).*
Ettinger (JAMA 1999, 282:637-646).*
Cohen (Arthritis & Rheumatism, 2008, 58:1299-1309).*
Brennan et al. (Seminars in Arthritis Rheumatism, 1997, 26:817-823).*
Kremer (Arthritis & Rheumatism, 1994, 37:316-328).*
McKinlay (Maturitas, 1996, 23:137-145).*
McKnight et al. (American Journal of Obstetrics and Gynecology, 2011, 205:353.e1-353e8).*
Smith et al. (CA: A Cancer Journal for Clinician, 2010, 60:99-119).*
Thomas et al. (Lancet Oncology, 2010, 11:275-280).*
Chawla et al. (Lancet Oncology, 2013, 14:901-908).*
A. Leibbrandt et al., "ESCI award lecture: from a little mouse to rationale medicine for bone loss", European Journal of Clinical Investigation, Oct. 2009, pp. 842-850, vol. 39, No. 10.
A. C. Bharti et al., "Ranking the role of RANK ligand in apoptosis", Apoptosis, An International Journal on Programmed Cell Death, Nov. 2004, pp. 677-690, vol. 9, No. 6.
Daniel Schramek et al., "Osteoclast differentiation factor RANKL control development of progestin-driven mammary cancer", Nature, Nov. 2010, pp. 98-102, vol. 468, No. 7320.
Georgiana K. Ellis et al., "Effect of denosumab on bone mineral density in women receiving adjuvant aromatase inhibitors for non-metastatic breast cancer: subgroup analyses of a phase 3 study", Breast Cancer Research and Treatment, Nov. 2009, pp. 81-87, vol. 118, No. 1.
Hye-Rim Park et al., "Expression of Osteoprotegerin and RANK Ligand in Breast Cancer Bone Metastasis", Journal of Korean Medical Science, Aug. 2003, pp. 541-546, vol. 18, No. 4.
J Canon et al., "Prevention of tumor growth and tumor-induced osteolysis by the RANKL inhibitor osteoprotegerin (OPG) is associated with significant improvement in survival using a mouse model of breast cancer bone metastasis", Bone, Jun. 2007, pp. S145, vol. 40, No. 6, Suppl. 2.
J Canon et al., "The RANKL inhibitor osteoprotegerin (OPG) inhibits tumor growth, prevents tumor-induced osteolysis, and significantly improves survival in a mouse model of breast cancer bone metastasis", European Journal of Cancer. Supplement, Nov. 2006, pp. 166-167, vol. 4, No. 12.
Jian Zhang et al., "Osteoprotegerin inhibits prostate cancer-induced osteoclastogenesis and prevents prostate tumor growth in the bone", Journal of Clinical Investigation, May 2001, pp. 1235-1244, vol. 107, No. 10.
Jude Canon et al., "P13 the RANKL inhibitor OPG-Fc delays the de novo establishment of breast cancer skeletal metastases in an MDA-MB-231 mouse model", Cancer Treatment Reviews, Jan. 2008, pp. 17, vol. 34.

(Continued)

*Primary Examiner* — Julie Wu
(74) *Attorney, Agent, or Firm* — Sughrue Mion, PLLC

(57) ABSTRACT

The present invention relates to a method of treating or preventing cancer in a subject comprising administering a therapeutically effective amount of a RANKL inhibitor to said patient.

Figure 1:
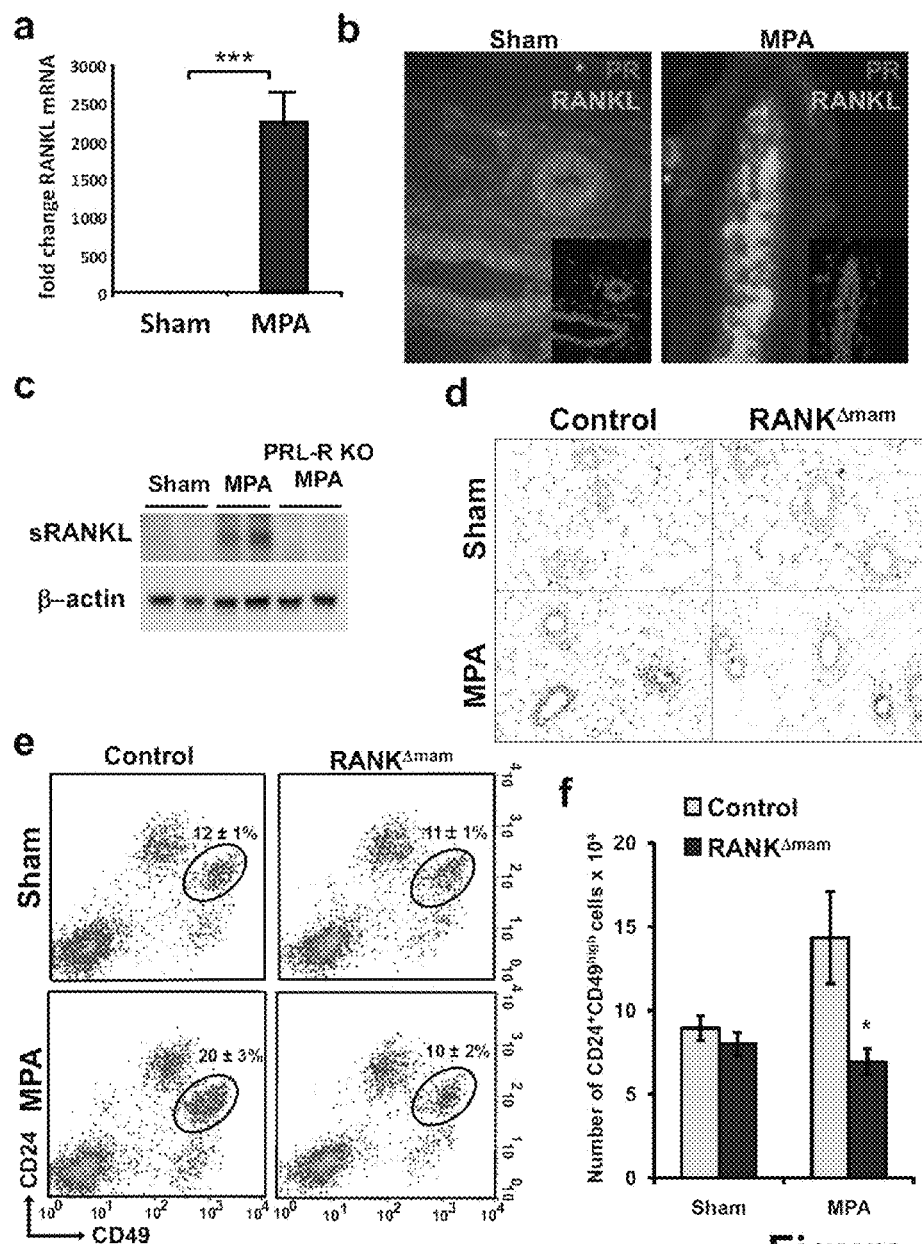

8 Claims, 20 Drawing Sheets
(20 of 20 Drawing Sheet(s) Filed in Color)
Specification includes a Sequence Listing.

(56) References Cited

OTHER PUBLICATIONS

M. Tometsko et al., "Efficacy of a RANKL inhibitor, OPG-Fc, relative to zoledronic acid to inhibit bone metastasis of a RANK-expressing human breast cancer cell line", Bone, Jul. 2010, pp. S325-S326, vol. 47, No. Suppl. 2.
M. Tometsko et al., "RANKL Inhibition Causes a Greater Suppression of Tumor-Induced Osteoclastogensis Than Zoledronate Treatment in Vivo and RANKL Rescues Osteoclasts from Zoledronate Killing in Vitro", Journal of Bone and Mineral Research, Sep. 2006, pp. S346, vol. 21, No. Suppl. 1.
Pamela M Holland et al., "Combined therapy with the RANKL inhibitor RANK-Fc and rhApo2L/TRAIL/dulanermin reduces bone lesions and skeletal tumor burden in a model of breast cancer skeletal metastasis", Cancer Biology and Therapy, Apr. 2010, pp. 539-550, vol. 9, No. 7.
Richard J Lee et al., "Treatment and prevention of bone complications from prostate cancer", Bone, Jun. 2010, pp. 88-95, vol. 48, No. 1.
Sam D Molyneux et al., "Prkar1a is an osteosarcoma tumor suppressor that defines a molecular subclass in mice", Journal of Clinical Investigation, Sep. 2010, pp. 3310-3325, vol. 120, No. 9.
Toru Akiyama et al., "Systemic RANK-Fc protein therapy is efficacious against primary osteosarcoma growth in a murince model via activity against osteoclasts", Journal of Pharmacy and Pharmacology, Apr. 2010, pp. 470-476, vol. 62, No. 4.
Xiaojun Wu et al., "RANKL regulates Fas Expression and Fas-Meditated Apoptosis in Osteoclasts", Journal of Bone and Mineral Research, Jan. 2005, pp. 107-116, vol. 20, No. 1.
Examination Report for Chilean Application No. 801-13 dated Aug. 4, 2014.
Beleut et al., "Two distinct mechanisms underlie progesterone-induced proliferation in the mammary gland", PNAS, 107(7):2989-2994 (2010).
Aldaz et al., "Medroxyprogesterone acetate accelerates the development and increases the incidence of mouse mammary tumors induced by dimethylbezanthracene", Carcinogenesis, 17(9):2069-2072 (1996).
Aliprantis et al., "NFATc1 in mice represses osteoprotegerin during osteoclastogenesis and dissociates systemic osteopenia from inflammation in cherubism", J. Clin. Invest., 118(11):3775-3789 (2008).
Asselin-Labat et al., "Control of mammary stem cell function by steroid hormone signalling", Nature, 465:798-803 (2010).
Bao et al., "Clinical Significance of Tumor Necrosis Factor Receptor Superfamily Member 11b Polymorphism in Prostate Cancer", Ann. Surg. Oncol., 17(6):1675-1681 (2010).
Cao et al., "IkappaB kinase alpha kinase activity is required for self-renewal of ErbB2/Her2-transformed mammary tumor-initiating cells", Proc. Natl. Acad. Sci., USA, 104(40):15852-15857 (2007).
Chen et al., "Expression of RANKL/RANK/OPG in primary and metastatic human prostate cancer as markers of disease stage and functional regulation", Cancer, 107(2):289-298 (2006).
Dontu et al., "In vitro propagation and transcriptional profiling of human mammary stem/progenitor cells", Genes Dev., 17:1253-1270 (2003).
Dougall et al., "RANK is essential for osteoclast and lymph node development", Genes Dev., 13:2412-2424 (1999).
Ewan et al., "Transforming growth factor-beta1 mediates cellular response to DNA damage in situ", Cancer Res., 62:5627-5631 (2002).
Fata et al., "The Osteoclast Differentiation factor osteoprotegerin-ligand is essential for mammary gland development", Cell, 103:41-50 (2000).
Findlay et al., "Circulating RANKL is inversely related to RANKL mRNA levels in bone in osteoarthritic males", Arthritis Res. Ther., 10:R2 (2008).
Freedman et al., "Cellular tumorigenicity in nude mice: correlation with cell growth in semi-solid medium", Cell, 3:355-359 (1974).
Gareus et al., "Normal epidermal differentiation but impaired skin barrier formation upon keratinocyte-restricted IKK1 ablation", Nat. Cell Biol., 96:461-469 (2007).
Hanada et al., "Central control of fever and female body temperature by RANKL/RANK", Nature, 462:505-509 (2009).
Hanahan et al., "The hallmarks of cancer", Cell, 100:57-70 (2000).
Jones et al., "Regulation of cancer cell migration and bone metastasis by RANKL", Nature, 440(30):692-696 (2006).
Jorgensen et al., "Bone loss in relation to serum levels of osteoprotegerin and nuclear factor-kappaB ligand: the Tromso Study", Osteoporos Int., 21:931-938 (2010).
Joshi et al., "Progesterone induces adult mammary stem cell expansion", Nature, 465:803-807 (2010).
Kim et al., "Receptor activator of NF-kappaB ligand regulates the proliferation of mammary epithelial cells via Id2", Mol. Cell. Biol., 266:1002-1013 (2006).
Kong et al., "OPGL is a key regulator of osteoclastogenesis, lympho-cyte development and lymph-node organogenesis", Nature, 397:315-323 (1999).
Lacey et al., "Osteoprotegerin ligand is a cytokine that regulates oseoclast differentiatoin and activation", Cell, 93:1635-176 (1998).
McTiernan et al., "Estrogen-plus-progestin use and mammographic density in postmenopausal women: Women's Health Initiative randomized trial", J. Natl. Cancer Inst., 97(18):1366-1376 (2005).
Menon et al., "Sensitivity and specificity of multimodal and ultrasound screening for ovarian cancer, and stage distribution of detected cancers: results of the prevalence screen of the UK Collaborative Trial of Ovarian Cancer Screening (UKCTOCS)", Lancet Oncol., 10:327-340 (2009).
Pece et al., "Biological and molecular heterogeneity of breast cancers correlates with their cancer stem cell content", Cell, 140:62-73 (2010).
Reid et al., "Breast Cancer cells stimulate oesteoprotegerin (OPG) production by endothelial cells through direct cell contract", Abstract No. XP002621521, Molecular Cancer, 8:49 (2009).
Robinson et al., "Inhibins and activins regulate mammary epithelial cell differentiation through mesenchymal-epithelial interactions", Development, 124:2701-2708 (1997).
Schett et al., "Soluble RANKL and risk of nontraumatic fracture", JAMA 291(9):1108-1113 (2004).
Shackleton et al., "Generation of a functional mammary gland from a single stem cell", Nature, 439:84-88 (2006).
Stingl et al., "Purification and unique properties of mammary epithelial stem cells", Nature, 439:993-997 (2006).
Tarutani et al., "Tissue-specific knockout of the mouse Pig-a gene reveals important roles for GPI-anchored proteins in skin development", Proc. Natl. Acad. Sci., USA, 94:7400-7405 (1997).
Terpos et al., "Soluble receptor activator of nuclear factor kB ligand-osteoprotegerin ratio predicts Survival in multiple myeloma: proposal for a novel prognostic index", Blood, 102(3):1064-1069 (2003).
Toshihiro et al., "Biochemical markers in bone metastasis", Abstract No. PX002621519, Database Accession No. NLM15272580, Cancer & chemotherapy, 31(7):1027-1033 (2004).
Examination Report for New Zealand Application No. 608207 dated Mar. 10, 2014.
Body et al., "A study of the biological receptor activator of nuclear factor-kappaB ligand inhibitor, denosumab, in patients with multiple myeloma or bone metastases from breast cancer", Clin. Cancer Res., 12:1221-1228 (2006).
Ellis et al., "Randomized trial of denosumab in patients receiving adjuvant aromatase inhibitors for nonmetastatic breast cancer", Journal of Clinical Oncology, 25(30):4875-4882 (2008).
Office Action, dated Jul. 21, 2015, issued in corresponding Japanese Patent Application No. 2013- 529652. English Translation.
Gonzalez-Suarez et al., "RANK Overexpression in Transgenic Mice with Mouse Mammary Tumor Virus Promoter-Controlled Rank Increases Proliferation and Impairs Alveolar Differentiation in the Mammary Epithelia and Disrupts Lumen Formation in Cultured Epithelial Acini," Molecular and Cellular Biology, 27(4):1442-1454 (2007).

\* cited by examiner a  7 days after DMBA b  22 days after DMBA

Densitometry
Fig. 1b
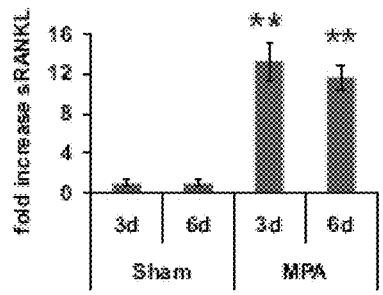
Fig. 1c
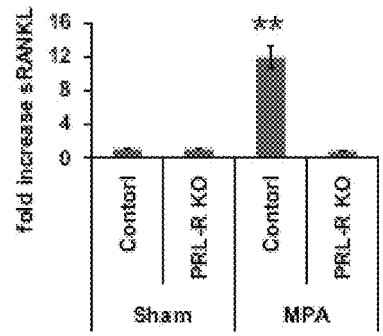
Fig. 3a
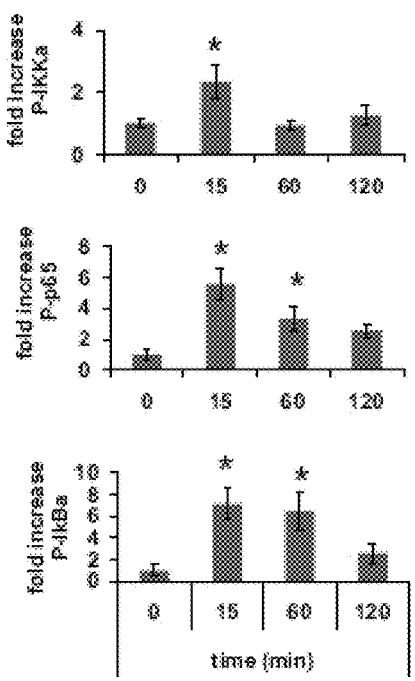
Fig. 3b
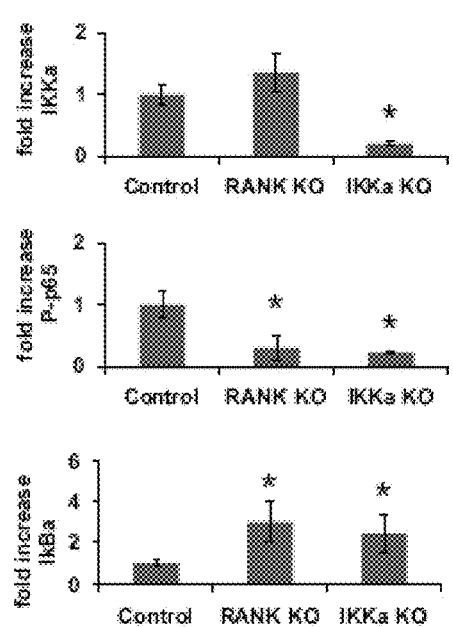
Figure 20

BREAST CANCER THERAPEUTICS

CROSS REFERENCE TO RELATED APPLICATIONS

This application is a National Stage of International Application No. PCT/EP2011/066511, filed on Sep. 22, 2011, claims priority from European Patent Application No. 10178346.2, the contents of which are incorporated herein by reference in their entirety.

The present invention relates to the field of cancer therapeutics.

ELLIS et al., Breast Cancer Research and Treatment, 118 (1) (2009): 81-87, describe the administration of Denosumab to increase bone mineral density in breast cancer patients during the treatment with aromatase inhibitor as anti-cancer agent.

TOMETSKO et al., Bone, 47 (2010): 325-326, relates to the role of RANK/RANKL in bone metastases. RANKL is said to be a critical mediator of osteoclast activity, which in turn favours tumour growth. Some breast and prostate cancer cell lines are disclosed to express RANK, thus having the ability to form bone metastases.

CANON et al., Bone, 40 (6) (2007):145, CANON et al., Europ. J. of Cancer, 4 (12) (2006): 166-167, CANON et al., Cancer Treatment Reviews, 34 (2008): 60, and TOMETSKO et al., J. Bone and Mineral Res., 21 (2006): 346 (Abstract) disclose the use of RANKL inhibitor OPG to treat tumour growth of cancer bone metastases.

HOLLAND et al., Cancer Biology and Therapy, 9 (7) (2010): 539-550, contains a comparison of administering a RANKL inhibitor (RANK-Fc) alone or together combination with an apoptosis-inducing ligand (rhApo2L) in the treatment of breast cancer skeletal metastases.

AKIYAMA et al., J. Pharmacy and Pharmacology, 62 (4) (2010): 470-476, relates to the administration of RANK-Fc in the treatment of osteosarcoma ZHANG et al., J. Clin. Invest., 107 (10) (2001): 1235-1244, relates to bone metastatic prostate cancer cells in vitro.

LEE et al., Bone, 48 (1) (2010): 88-95 relates to bone metastasis of prostate cancer. This document summarizes different pharmaceutical agents and studies investigating the effects of metastatic prostate cancer.

LEIBBRANDT et al., Europ. J. of Clin. Invest., 39 (10) (2009): 842-850, is a review article on the functions of RANK, RANKL and OPG on osteoblasts and osteoclasts, and their involvement in bone metastasis formation.

WO 99/53942 discloses the use of OPG in the treatment of cardiovascular disease.

WU et al., J. Bone and Mineral Res., 20 (1) (2005): 107-116 discloses RANKL as regulator of Fas-mediated apoptosis of osteoclasts.

BHARTI et al., Apoptosis, 9 (6) (2004): 677-690, relates the role of RANKL in apoptosis of osteoclast precursors.

MOLYNEUX et al., J. Clin. Invest., 120 (9) (2010): 3310-3325, relates to research on Prkarla as bone tumour suppressor gene, which is capable of inducing RANKL overexpression during osteosarcoma tumourigenesis.

PARK et al., J. Korean Med. Sci., 18 (4) (2003): 541-546, contains a discussion of the role of OPG and RANKL in breast cancer bone metastasis.

It is a goal of the invention to provide alternative anti-cancer therapies that do not suffer from this drawback.

Receptor Activator of NF-κB Ligand (RANKL, also known as ODF, TRANCE, OPGL, TNFSF11) and its receptor RANK (TRANCE-R, TNFRSF11A) are essential for the development and activation of osteoclasts. RANKL inhibition was approved for potentially millions of patients to prevent bone loss. RANK and RANKL have been cloned and characterized (U.S. Pat. No. 6,017,729, EP 0 873 998, EP 0 911 342, U.S. Pat. No. 5,843,678, WO 98/46751, WO 98/54201). Both RANKL and RANK expression have been observed in primary breast cancers in humans and breast cancer cells lines and it has been proposed that the RANKL/RANK system can regulate bone metastases of epithelial tumors[14] without an effect on proliferation or death susceptibility.

US 2008/107597 and WO 2010/022120 A1 describe anti-RANKL antibodies and their use for inhibiting bone loss associated with a multitude of diseases or for the treatment of "RANKL-associated diseases".

In WO 02/098362 the treatment of cancer in non-hypercalcemic patients with a RANK antagonist is proposed. However no therapy was developed and this patent family was finally abandoned.

Established uses of RANKL for treating diseases associated with bone and calcium metabolism and inflammatory conditions are described e.g. in WO 2007/128564.

Breast cancer is one of the most common cancers in humans and will on average affect up to one in eight women in their life time in the US and Europe. The Women's Health Initiative (WHI) and the Million Women Study have shown that hormone replacement therapy (HRT) is associated with an increased risk of incident and fatal breast cancer. In particular synthetic progesterone derivatives (progestins) such as medroxyprogesterone acetate (MPA), used in millions of women for HRT and contraceptives, markedly increase the risk of developing breast cancer.

Estrogene as well as progesterone including its synthetic derivatives (progestins) are used in combined hormone replacement therapies (HRT) in postmenopausal women to ameliorate menopausal symptoms. Estrogene and progestins may also be used as hormonal contraceptives.

Tamoxifen is an antagonist of the estrogen receptor in breast tissue. It is a standard endocrine (anti-estrogen) therapy for hormone-positive early breast cancer in postmenopausal women. It would also inhibit hormone replacement therapies by blocking the estrogen receptor.

It is a goal of the present application to provide therapeutic methods and means for preventing or treating cancer.

The present invention relates to the specific role of RANKL in cancer and methods and means to interfere in the cancer associated RANKL mechanism for therapeutic or prophylactic purposes. It was found that RANKL is responsible for protecting cells from cancerogenous mutations as it prevents cell death after such mutations induced by DNA damage. Survival of cells despite transforming mutations is one key property of cancer cells. The newly discovered role of RANKL in this activity allows the inhibition of RANKL activity to treat and prevent cancer development and progression. Although RANKL involvement was known during bone metastasis formation due to effects on osteoclast and osteoblasts, it was not known that RANKL can have a direct effect on cancer cell formation.

The present invention relates to a cancer therapy using a RANKL inhibitor as active agent, especially in the prevention or treatment of primary tumours apart from metastatic cancer cells.

According to the present invention a cancer therapy is to be understood as the reduction of cancer cells in the body of a patient or at least the prevention of further progression of the disease. RANKL inhibitors include antibodies widely known e.g. from US 2008/107597, WO 2010/022120 A1, U.S. Pat. No. 6,740,522, U.S. Pat. No. 7,411,050, EP 2003203 A1, or polypeptide inhibitors disclosed in US 2004/167072. Any of these prior RANKL inhibitors can be used according to the present invention.

RANKL is a known ligand of cell surface receptor RANK that regulates function of dendritic cells and osteoclasts. According to the present invention, a further mechanism in the development of cancer has been discovered. RANKL drives hormone-influenced cancer development. Such hormones may be of the normal hormonal background in any individual or may have been artificially administered (such as in hormone replacement therapies, in menopause treatment or as contraceptive). Furthermore, the cellular mechanism and activity of this ligand in cancer has been investigated and characterized.

The effect of RANKL, "RANKL activity", includes binding of RANKL to RANK and its resulting activation. RANK in turn further activates IKKα, IκBα, P-NFκB and cyclinD1 as well as the Id2-p21, MAPK Erk and p38 pathway. Modifying activity of any of these factors can be used for a therapeutic or prophylactic method or to reduce cancer cell viability. Most of these proteins are intracellular and it is possible to inhibit their function by intracellular inhibition of their activity or expression such as by RNAi. RANKL and RANK are extracellular targets but may also be targeted intracellular (e.g. by RNAi).

According to the invention it was found that in vivo administration of progestins such as MPA triggers massive induction of the key osteoclast differentiation factor Receptor Activator of NF-B Ligand (RANKL) in cells. Inhibition or inactivation of RANKL or its receptor RANK in these cells prevents progestin-induced proliferation. Importantly, RANKL/RANK inhibition results in a markedly reduced incidence and delayed onset of progestin-driven cancer and reduced self-renewal capacity of cancer stem cells. Although RANKL is known to influence bone metastasis of tumors, the present invention provides for the first time the possibility to treat cancer in general and cancer independent of metastasis, which metastasis is not target of the inventive treatment. Preferably the cancer is a primary tumor. The cancer may be non-metastatic.

In prior publications (WO 02/098362) it was suggested to use RANK antagonists in cancer therapy. However no therapy was finally developed based on this suggestion. According to the present invention, particular preferred targets are cells dependent on hormone signalling for growth. A significant factor in RANK/RANKL driven cancer development is the hormonal background. According to the invention RANK/RANKL's cancerogenous effect has been associated with sexual hormones, in particular progesterone and its derivatives (progestins), that are widely administered to females in hormone replacement therapies or as contraceptives. Therefore a RANK/RANKL antagonizing therapy according to a preferred embodiment is for treating patients with elevated sexual hormones or of their functional derivatives. One cancer treated or prevented according to the present invention is breast cancer, including primary breast cancer.

In preferred embodiments the cancer is a cancer dependent on hormones for growth. Such hormones may be sexual hormones, such as female sexual hormones like progesterone or estrogen. The cancer cells may have hormone receptors, especially progesterone receptors and/or estrogene receptors. Examples of estrogene receptors are ESR1 (comprising ER alpha chains), ESR2 (comprising ER-beta chains) or heteromeric receptors, such as of mixed ER-alpha and ER-beta chains. Presence of such receptors may indicate a requirement of hormone signalling in the cell. In particular, this signalling may be RANKL-mediated. Preferably the hormone signalling is mediated by the progesterone receptor. In special embodiments the cancer comprises cancer cells with a progesterone receptor but without functional estrogene receptor.

Activation of RANKL by hormones protects the cancer or a pre-cancerous cell from DNA damage induced cell death. Thus these hormones may support cancer via increased RANKL activity. Preferred types of cancer diagnosed according to the present invention are cancers with sexual hormone dependency during development, especially breast cancer or prostate cancer. Further types of cancer include Hodgkin's lymphoma; non-Hodgkin's lymphoma; B-cell acute lymphoblastic leukemia/lymphoma; T-cell acute lymphoblastic leukemia/lymphoma; peripheral T-cell leukemia, adult T-cell leukemia/T-cell lymphoma; NK cell tumor; large granular lymphocytic leukemia; Langerhans cell histiocytosis; myeloid neoplasia; acute myelogenous leukemia; acute promyelocytic leukemia; acute myelomonocytic leukemia; acute monocytic leukemia; a myelodysplastic syndrome; and a chronic myeloproliferative disorder. In particular preferred the cancer is selected from lung cancer, breast cancer, mammary cancer, melanoma, sarcoma, prostate cancer, head and neck cancer, cancer of unknown primary origin, lymphoma, leukemia, kidney cancer, and gastrointestinal cancer. Preferably the cancer is a hormone driven-cancer like breast or prostate cancer. Such hormones may be female sexual hormones like estrogen or progesterone, or artificial functional equivalents thereof like progestins or other factors known to induce RANKL such as PTHrP (Parathyroid hormone-related protein) or Vitamin D. The cancer may be of epithelial origin. Preferably the cancer is treated or prevented in its origin tissue, such as in the breast in the case of breast or mammary cancer or in the prostate for prostate cancer.

According to the invention the cancer may be a primary cancer. As shown herein a primary cancerous development can be prevented or delayed by inhibiting RANKL activity. Therefore the primary cancer can be treated or prevented. In addition it is also possible to prevent or treat the development of re-occurring cancer.

According to one embodiment the invention provides a RANKL inhibitor for use in the treatment or prevention of cancer in a patient, wherein the patient has received a hormone treatment, preferably a hormone replacement therapy, preferably with estrogene, progesterone or a progestin, or a hormone contraceptive.

"Treatment" shall be construed as a beneficial effect on cancer patients, in particular as a reduction of cancer cells, including preventing further progression of cancer, but not necessarily in an absolute curative sense, which is of course possible but not necessarily required by the invention.

Similar, "preventing" shall not be construed as an absolute success to always prevent the onset of cancer, but as a relative reduction of the risk of developing cancer in a patient or of delaying onset of cancer, i.e. as a prophylactic treatment. The prevention of cancer is a particular advantage of the present invention. Since RANKL-induced protection against apoptosis is a fundamental step in the development of cancer, it is now possible to inhibit this step in cancerous developments and prevent for a certain time or delay cancer manifestation. The treatment or prevention according to the present invention can be used to treat benign tumors or nodules and thus inhibit further development in cancer formation.

The normal hormonal levels of a patient may usually be sufficient to trigger the RANKL pathway that has been involved with cancer development according to the present invention. At certain conditions hormone level may be increased in a patient, be it for natural or artificial causes. Such increased hormone level may increase the RANKL associated cancer development and progression and therefore in a preferred embodiment the patient to be treated according to the present invention has increased hormone levels, e.g. blood concentrations, in particular of sexual hormones such as progesterone (or the synthetic functional analogons, progestines) or estrogenes. The administration of a female sexual hormones to a patient, be it for a hormone replacement therapy or as hormone contraceptive (particular progesterone and its derivatives) increases the risk of cancer via the RANKL pathway, in particular of hormone driven cancers such as breast cancer or prostate cancer. Further, any deregulation of the endogenous progesterone system such as in pre-menopause may increase the risk of cancer. In turn, administrating a RANKL inhibitor can decrease the risk of breast cancer or be used to treat a breast cancer. Mechanistically, RANKL activity protects breast cancer cells from apoptosis and increases breast cancer survival in view of cancerogenic mutations. Reducing RANKL activity therefore prevents this protective effect and results in increased cancer cell death.

The patient might have or might have had a therapy with sexual hormones. It was found according to the present invention that RANKL activity in cancer development is influenced by sexual hormones, in particular by estrogenes or progesteron or its dervatives (progestins). Therefore, in preferred embodiments the patient is treated by a hormone, preferably receives hormone replacement therapy, preferably with estrogene, progesterone or a progestin, or with a hormone contraceptive. Examples of progestins are medroxyprogesterone (or its acetate, e.g. the 17-acetate), norethisterone, ethisterone, norethynodrel, norethindrone acetate, ethynodiol diacetate, levonorgestrel, norgestrel, desogestrel, gestodene, norgestimate, drospirenone, dienogest, nesterone, nomegestrol acetate, trimegestrone, tanaproget, megestrol acetate, pranone, etonogestrel. The hormone or derivative preferably has progestinic effects. In particular the hormone may induce RANKL.

In hormone replacement therapies or by using hormone contraceptives, the hormone level, in general of sexual hormones, is upregulated leading to increased progesterone levels that could be tied to development of cancer via the RANKL pathway according to the present invention. Therefore, patients which receive or have been treated by a hormone or hormone contraceptive are at an increased risk of developing breast cancer. For these patients, administering a RANKL inhibitor is particularly effective for treating or preventing cancer, cancer development or cancer progression.

In particular high progestin and/or progesterone levels that may be found in a patient to be treated are e.g. serum concentration or at least 0.2 ng/ml, preferably at least 0.3 ng/ml.

A "RANKL inhibitor" is to be understood as any compound or agent, that reduces RANKL activity. It includes any RANKL ligand, in particular anti-RANKL-antibodies, that inactivates free RANKL and prevents competitively its binding to and activation of RANK. Further RANKL inhibitors include RANK antagonists that block RANK, RANKLs cellular receptor. Furthermore, any factor in RANKLs signalling pathway, including RANKL itself, RANK, IKKα, IκBα, P-NFκB, cyclinD1 (NFκB pathway inhibition), Id2, MAPK Erk and p38 can be antagonized or p21 increased or agonized (Id2 pathway inhibition) to prevent RANKL signalling and reduce RANKL activity. The Id2 pathway functions as a transcriptional repressor of p21, on of the major cyclin-dependent kinase inhibitors, which inhibits cell cycle progression. Therefore, the Id2 pathway has to be inhibited for p21 to be upregulated hence stopping proliferation.

A RANKL inhibitor can inhibit or antagonize any one of RANKL itself, RANK, IKKα, IκBα, P-NFκB, cyclinD1, Id2, MAPK Erk or p38 or increase or agonize p21 or any combination thereof, preferably of at least 2, 3, 4, 5, or all of these factors, in particular preferred with RANKL. A RANKL inhibitor may be any compound that lowers RANKL concentration, in particular serum concentrations, or lower RANKL expression. A RANKL inhibitor may further lower RANK concentration on cell surface, in particular cancer cell surface, and/or lower RANK expression and/or lower RANK activation in response to RANKL binding. A RANKL inhibitor may further lower intracellular concentrations and/or expression and/or activation of IKKα. A RANKL inhibitor may further lower intracellular concentrations and/or expression and/or activation of IκBα. A RANKL inhibitor may further lower intracellular concentrations centrations and/or expression and/or activation of P-NFκB. A RANKL inhibitor may further lower intracellular concentrations and/or expression and/or activation of cyclinD1. A RANKL inhibitor may further lower intracellular concentrations and/or expression and/or activation of Id2. A RANKL inhibitor may further increase intracellular concentrations and/or expression and/or activation of p21. A RANKL inhibitor may further lower intracellular concentrations and/or expression and/or activation of MAPK Erk. A RANKL inhibitor may further lower intracellular concentrations and/or expression and/or activation of p38.

For antagonizing cellular factors preferably siRNA molecules are administered to reduce the expression and function of these factors. RNA interference (RNAi) is a mechanism to suppress gene expression in a sequence specific manner. RNA interference (RNAi) is highly effective methodology for suppression of specific gene function in eukaryotic cells. When applied to cells and organisms, RNAi entails the degradation of target mRNA upon transfection of short interfering RNA (siRNA) oligos or short-hairpin RNA (shRNA) encoding vectors. Various methods of RNAi have been described and are generally known for the altering gene expression in plant cells, drosophila and human melanoma cells as is described for example in US 2002/0162126 and US 2002/0173478. The siRNA for use in the methods and compositions of the invention are selected to target a desired molecule of the RANKL signaling pathway or combinations of such molecules. In this manner they are targeted to various RNAs corresponding to a target gene. It is understood by one of skill in the art that the siRNA as herein described may also include altered siR-NA t that is a hybrid DNA/RNA construct or any equivalent thereof, double-stranded RNA, microRNA (miRNA), as well as siRNA forms such as siRNA duplications, small hairpin RNA (shRNA) in viral and non-viral vectors and siRNA or shRNA in carriers. RANKL RNAi is e.g. described in WO 2005/028633.

There exists several methods in the art for inhibiting gene expression using RNAi such as described for example in WO 02/055692, WO 02/055693, EP 1 144 623 B1 and WO 03/074654. By using a siRNA therapy any cellular factor can be targeted and inhibited for the inventive RANKL antagonizing and inhibiting therapy. Therefore, any such compound can be used as a RANKL inhibitor.

In preferred embodiments the RANKL inhibitor is a RANKL or RANK ligand, preferably an anti-RANKL antibody, such as Denosumab, or as disclosed in US 2008/107597. "Anti-RANKL-antibody" includes any functional equivalents and derivatives therof, including antibody fragments such as Fab, F(ab)2, Fv, or single chain antibodies (scAb). Antibodies specifically binding the RANKL activity associated proteins and factors, especially RANKL and RANK and any proteins in the RANKL signalling pathway, are also encompassed by the invention. The antibodies may be produced by immunization with full-length protein, soluble forms of the protein, or a fragment thereof. The antibodies of the invention may be polyclonal or monoclonal, or may be recombinant antibodies, such as chimeric antibodies wherein the murine constant regions on light and heavy chains are replaced by human sequences, or CDR-grafted antibodies wherein only the complementary determining regions are of murine origin. Antibodies of the invention may also be human antibodies prepared, for example, by immunization of transgenic animals capable of producing human antibodies (WO 93/12227). The antibodies are useful for detecting RANKL in biological samples, thereby allowing the identification of cells or tissues which produce the protein in addition, antibodies which bind to RANKL (and block interaction with other binding compounds) have therapeutic use as RANKL inhibitor.

RANKL inhibitors may be suitable and used for reducing the free RANKL concentration in the circulation of a patient. RANK is not the only natural receptor for RANKL. Osteoprotegin (OPG) is a secreted decoy receptor that can reduce the RANKL activity (binding of RANKL to RANK and its signaling pathway via IKKα, Ikα, P-NFκB and cyclinD1 or via Id2-p21, MAPK Erk and p38). Therefore OPG may be administered as RANKL inhibitor. Furthermore RANK or a soluble form thereof itself may be used as RANKL ligand and inhibitor to reduce the free serum concentration of RANKL.

The inhibitor is usually administered in a therapeutically effective amount, an amount that reduces RANKL activity to significantly decrease cancer cell viability. In particular embodiments the RANKL activity may be suppressed to normal levels of an average person, furthermore, the RANKL activity may be reduced below average levels. Preferably the RANKL activity is reduced by at least 25%, by at least 30%, by at least 40%, by at least 50%, by at least 60%, by at least 70% by at least 80% or by at least 90%. In preferred embodiments this reduction equates to RANKL serum levels.

The inhibitor may be used in combination with or for priming a further anti-cancer therapy, preferably a radiation- or chemotherapy. According to this aspect of the present invention a method for increasing the efficacy of cancer therapy in a subject is provided, comprising administering to a subject in need of an effective amount of an RANKL inhibitor, wherein said subject is also being administered a cancer therapy selected from the group consisting of small-molecule drugs, angiogenesis inhibitors, tumor vaccine, chemotherapy, immunotherapy, radiation therapy, gene therapy and combinations thereof.

RANKL acts as a protective agent, immunizing cancer cells against DNA damage associated cell death. By reducing RANKL activity and therefore reducing RANKLs protective effect on cancer, the cells become more susceptible to DNA damage. Therefore, in a preferred embodiment a cancer is treated in addition with a RANKL inhibitor and a further anti-cancer therapy that induces further cell damage such as radiation or chemotherapies. Preferably such further cancer therapies are specific for cancer in a certain tissue, like breast, e.g. by administering localised a chemotherapeutic agent or a homing agent that targets the tissue cancer cells and induces further DNA damage either by radiation or a chemotherapeutic agent.

According to this embodiment the present invention relates also to a kit comprising a chemotherapeutic agent and a RANKL inhibitor.

According to a further embodiment, a RANKL inhibitor is provided for use in combination with a hormone replacement therapy or for use in combination with a hormone contraceptive, in particular to reduce the risk of developing breast cancer.

The patient is preferably a mammal, in particular preferred a primate, even more preferred a human, in particular a female. The patient might have or might have had a therapy with hormones, in particular female sexual hormones. Such a past therapy might have been in the past 5, 4, 3, 2, years or past 36, 32, 30, 28, 26, 24, 22, 20, 18, 16, 14, 12, 10, 8, 7, 6, 5, 4, 3, 2, or 1, month(s). Patients, in particular females, receiving a hormone replacement therapy or are taking a hormone contraceptive, in particular a progesterone or a progestine are at an increased risk to develop cancer. To reduce this increased risk, the present invention provides the combined use of a RANKL inhibitor as described above.

The present invention further provides a method of reducing RANKL activity in a cancer patient comprising administering a RANKL inhibitor to said patient.

In a further aspect the invention relates to a method of reducing the amount of cancer cells in a patient comprising administering a RANKL inhibitor to said patient.

Furthermore the invention teaches a method of increasing cell death due to DNA damage of a cell comprising inhibiting RANK or RANKL or IKK-alpha or IkB-alpha, P-NF-kappa-B or CyclinD1 or Id2 or MAPK Erk or p38 or increasing p21 or any combination thereof, in particular a combination with inhibiting RANKL, in said cell, preferably by administering a RANKL inhibitor to said cell. The cell receiving the inventive treatment may be a tissue cell wherein hormone dependent cancers may develop, especially the breast (especially for prophylactic methods) or a cancer cell. Furthermore said cell can be an epithelial cell or a cancer stem cell. Especially cancer of epithelial origin can be effectively treated by the inventive methods. In particular preferred embodiments the cancer is of mammary gland epithelial cells. Furthermore RANKL inhibition as a significant effect on cancer stem cells and can prevent or reduce cancer comprising such stem cells.

According to preferred therapeutic or preventive methods characterized in that the patient has received a hormone treatment, preferably a hormone replacement therapy, preferably with progesterone or a progestin, or a hormone contraceptive, such as described above.

As mentioned above, hormone treatment, in particular with female sexual hormones increases the risk of breast cancer and therefore, in a inventive therapeutical preventive method preferably the patient has been treated with such a hormone therapy previously or during the inventive therapeutic method. Previous administrations of hormones may have been in the past 1, 2, 3, 4 or 5 years or more.

In a further aspect the present invention provides a pharmaceutical composition comprising a RANKL inhibitor and a hormone or derivative thereof, selected from progesterone or a progestin, or a hormone contraceptive.

As mentioned, RANKL inhibition can reduce the risk of developing cancer by female sexual hormones, in particular of estrogene, progesterone or progestins. Therefore, it is advised to administer such hormones together with the RANKL inhibitor provided by the present invention. Such hormones might be used for hormone replacement therapies or as hormonal contraceptives.

Most common types of hormonal contraceptive formulations include both an estrogen and a progestin, or are progestogen-only formulations which contain only progesterone or one of its synthetic analogues (progestins). In order to reduce the risk of hormone dependent cancer development, the present invention provides a combined use of hormone therapeutics, including female sexual hormone contraceptives, together with a RANKL inhibitor.

Pharmaceutical compositions or formulations for therapeutic or prophylactic use may comprise a pharmaceutically acceptable diluent, carrier, solubilizer, emulsifier, preservative and/or adjuvant. The invention also provides for pharmaceutical compositions comprising a therapeutically effective amount of an RANKL inhibitor. The term "therapeutically effective amount" means an amount which provides a therapeutic effect for a specified condition and route of administration. The composition may be in a liquid or lyophilized form and comprises a diluent (Tris, acetate or phosphate buffers) having various pH values and ionic strengths, solubilizer such as Tween or Polysorbate, carriers such as human serum albumin or gelatin, preservatives such as thimerosal or benzyl alcohol, and antioxidants such as ascrobic acid or sodium metabisulfite. Selection of a particular composition will depend upon a number of factors, including the condition being treated, the route of administration and the pharmacokinetic parameters desired. siRNA formulations are preferably administered in liposome formulations.

The present invention also relates to a kit comprising a hormone therapeutic, as described above, and a RANKL inhibitor. Such a kit may allow separate administration of the hormone therapeutic and the RANKL inhibitor.

Also encompassed are compositions comprising RANKL inhibitors modified with water soluble polymers to increase solubility, stability, plasma half-life and bioavailability. Compositions may also comprise incorporation of RANKL inhibitors into liposomes, microemulsions, micelles or vesicles for controlled delivery over an extended period of time. Soluble RANKL inhibitors may be formulated into microparticles suitable for pulmonary administration.

Compositions of the invention may be administered by injection, either subcutaneous, intravenous or intramuscular, or by oral, nasal, pulmonary or rectal administration. The route of administration eventually chosen will depend upon a number of factors and may be ascertained by one skilled in the art.

The invention also provides for pharmaceutical compositions comprising a therapeutically effective amount of the anti-RANKL inhibitory nucleic acids (siRNA) of the invention together with a pharmaceutically acceptable adjuvant. Nucleic acid compositions will be suitable for the delivery of part or all of the coding region of RANKL or any protein in the RANKL signalling pathway as described above and/or flanking regions to cells and tissues as part of an anti-sense therapy regimen.

In preferred embodiments the present invention is defined as follows:

1. Method of treating or preventing cancer in a subject comprising administering a therapeutically effective amount of a RANKL inhibitor to said patient.
2. Method of increasing cancer cell apoptosis comprising administering a RANKL inhibitor to said cancer cell.
3. Method according to definition 1, wherein the cancer is breast cancer or prostate cancer or according to definition 2 wherein the cancer cell is a breast cancer cell or a prostate cancer cell.
4. Method of any one of definitions 1 to 3, wherein the cancer comprises cancer cells with sexual hormone receptors, preferably progesterone or estrogene receptors.
5. Method of definition 1 to 4, wherein the cancer is a primary cancer or the cancer cell is a cell of a primary cancer.
6. A RANKL inhibitor for use in the treatment or prevention of hormone dependent cancer in a patient, preferably wherein the cancer comprises cancer cells with sexual hormone receptors, preferably progesterone or estrogene receptors.
7. Inhibitor of definition 6, wherein the patient has received a hormone treatment, preferably a hormone replacement therapy, preferably with progesterone or a progestin, or a hormone contraceptive.
8. Inhibitor according to definition 6 or 7, characterized in that the cancer is breast, mammary or prostate cancer.
9. Inhibitor according to any one of definitions 6 to 8, characterized in that the cancer is of epithelial cell origin.
10. Inhibitor according to any one of definitions 6 to 9 in combination with or for priming a further anti-cancer therapy, preferably a radiation- or chemotherapy.
11. Inhibitor according to any one of definitions 6 to 10 for treating or preventing a primary cancer or for treating or preventing reoccurence of a cancer.
12. A RANKL inhibitor for use in combination with a hormone therapy, preferably of sexual hormones, in particular a hormone replacement therapy or for use in combination with a hormone contraceptive.
13. Inhibitor according to any one of definitions 6 to 12 for reducing the risk of developing cancer.
14. A method of reducing RANKL activity in a cancer patient comprising administering a RANKL inhibitor to said patient.
15. A method of reducing the amount of cancer cells in a patient comprising administering a RANKL inhibitor to said patient.
16. A method of increasing cell death due to DNA damage of a cell comprising inhibiting RANK or RANKL or IKK-alpha in said cell, preferably by administering a RANKL inhibitor to said cell.
17. Method of any one of definitions 14 to 16, characterized in that the patient or cell has received a hormone treatment.
18. Method of any one of definitions 14 to 17, wherein the hormone is progesterone or a progestin.
19. Method of any one of definitions 14 to 23, wherein hormone treatment includes a hormone replacement therapy or administration of a hormone contraceptive.
20. Inhibitor or method of any one of definitions 1 to 19, wherein the RANKL inhibitor is a RANKL or RANK ligand or a siR-NA.
21. Inhibitor or method of definition 20, wherein RANKL inhibitor is an anti-RANKL antibody.
22. Inhibitor or method of definition 21, wherein the anti-RANKL antibody is Denosumab.
23. Inhibitor or method of any one of definitions 1 to 22, wherein said cell is a breast tissue cell or breast cancer cell or the cancer comprises cancerous cells selected from a breast tissue cell or breast cancer cell.
24. Inhibitor or method of any one of definitions 1 to 23, wherein said cell is an epithelial cell or a basal cancer cell or a cancer stem cell or the cancer comprises cancerous cells selected from an epithelial cell or a basal cancer cell or a cancer stem cell.

25. Pharmaceutical composition comprising a RANKL inhibitor and a hormone or derivative thereof selected from estrogene, progesterone or a progestin or a hormone contraceptive.
26. Composition of definition 25 further comprising a pharmaceutically acceptable diluent, carrier, solubilizer, emulsifier, preservative and/or adjuvant.
27. Composition of definition 25 or 26 for use in a hormone therapy.
28. Composition of definition 27, wherein the hormone therapy is contraception or a hormone replacement therapy.
29. Kit comprising a chemotherapeutic agent and a RANKL inhibitor.
30. Kit comprising a RANKL inhibitor and a hormone or derivative thereof, selected from estrogene, progesterone, or a progestin or a hormone contraceptive.

The present invention is further illustrated by the following figures and examples, without being limited to such specific examples.

FIGURES

The patent or application file contains at least one drawing executed in color. Copies of this patent or patent application publication with color drawings will be provided by the Office upon request and payment of the necessary fee.

FIG. 1. The progesterone-derivative MPA triggers in vivo RANKL expression and mammary epithelial cell proliferation via RANK.

a,b, Induction of RANKL expression by the progesterone-derivative MPA. Nulliparous wild type females were s.c. implanted with slow-release MPA pellets or treated with surgery sham. a, RANKL mRNA was determined in purified mammary epithelial cells by qRT-PCR three days after implantation. Data are shown as fold change compared to sham treatment (+/−sem) (n=3). b, In situ Ki67 immunostaining of progesterone receptor (PR, red) and RANKL (green) in mammary epithelial cells after 3d MPA treatment. c, Induction of soluble RANKL protein assayed on isolated mammary gland epithelial cells from control, but not in prolactin receptor mutant (PRL-R KO) females on day 3 after s.c. MPA implantation. Mammary glands from sham operated control litter-mates and PRL-R KO females are shown as controls. d, Epithelial proliferation in mammary glands of control littermates and RANK$^{\Delta mam}$ females 3 days after sham treatment and MPA implantation. Proliferation was determined by in situ Ki67 immunostaining. e,f, Marked increase of the stem cell-enriched CD24$^+$CD49$^{high}$ population (MaSC) in MPA-treated mammary glands in control but not in RANK$^{\Delta mam}$ mammary glands. e, Representative FACS profiles showing CD24 and CD49 expression of lineage negative (CD31$^-$ (endothelial cells) CD45$^-$ (hematopoietic cells) TER199$^-$ (erythroid cells)) of mammary MaSCs from MPA- or sham-treated 8-week old virgin females. f, Quantification of MaSC-enriched CD24$^+$CD49$^{high}$ population from mammary glands of MPA- or sham-treated virgin RANK$^{\Delta mam}$ and littermate control females. For all MaSCs experiments mice were treated with MPA for 3 days. n=4 per group+/−sem. *P<0.05; ***P<0.001 (Student's t-test).

Figure 2:
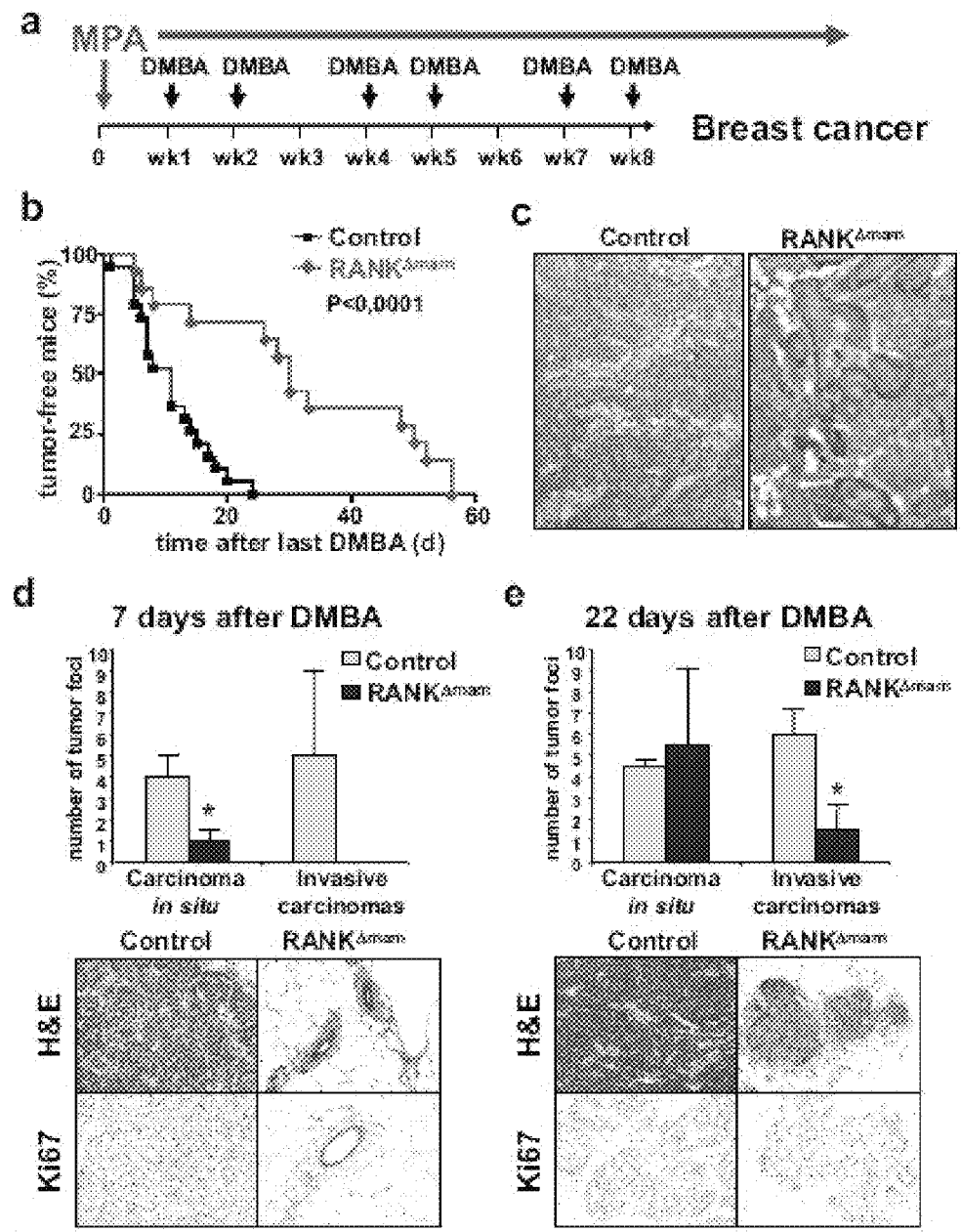

FIG. 2. RANK controls the incidence and onset of progestin-driven mammary cancer.

a, MPA/DMBA carcinogenesis scheme. Nulliparous, six-week old female mice were s.c. implanted with MPA pellets and treated orally with DMBA as indicated for 8 week. b, Onset of palpable mammary tumors in MMTV-Cre rank$^{floxed/\Delta}$ females (RANK$^{\Delta mam}$) (n=14) and age-matched littermate control females (n=19) treated with MPA pellets and DMBA as indicated in FIG. 2a. Data are shown as percentage of tumor free mice after the last DMBA challenge. Median tumor onset for controls was 11 days after last DMBA treatment and 30 days for RANK$^{\Delta mam}$ females. c, Representative histological sections of mammary tumors isolated from control littermate and RANK$^{\Delta mam}$ females 22 days after the last DMBA treatment. Cytokeratin5 staining is shown. Magnifications×20 d,e, Numbers of carcinomas in situ and invasive mammary cancers in control and RANK$^{\Delta mam}$ females on day 7 (d) and day 22 (e) after the final DMBA treatment. Data are shown as mean values per mouse+/−sem. n=3 mice per genotype. All 10 mammary glands were analysed for each mouse. *P<0.05 (Student's t-test). Bottom panels show representative histological sections with typical invasive adenocarcinomas in the control females. For RANK$^{\Delta mam}$ females, normal acinar morphology (day 7) and a carcinoma in situ (day 22) are shown. H&E stained sections and immunostaining for the proliferation marker Ki67 are shown. Magnifications×20.

Figure 3:
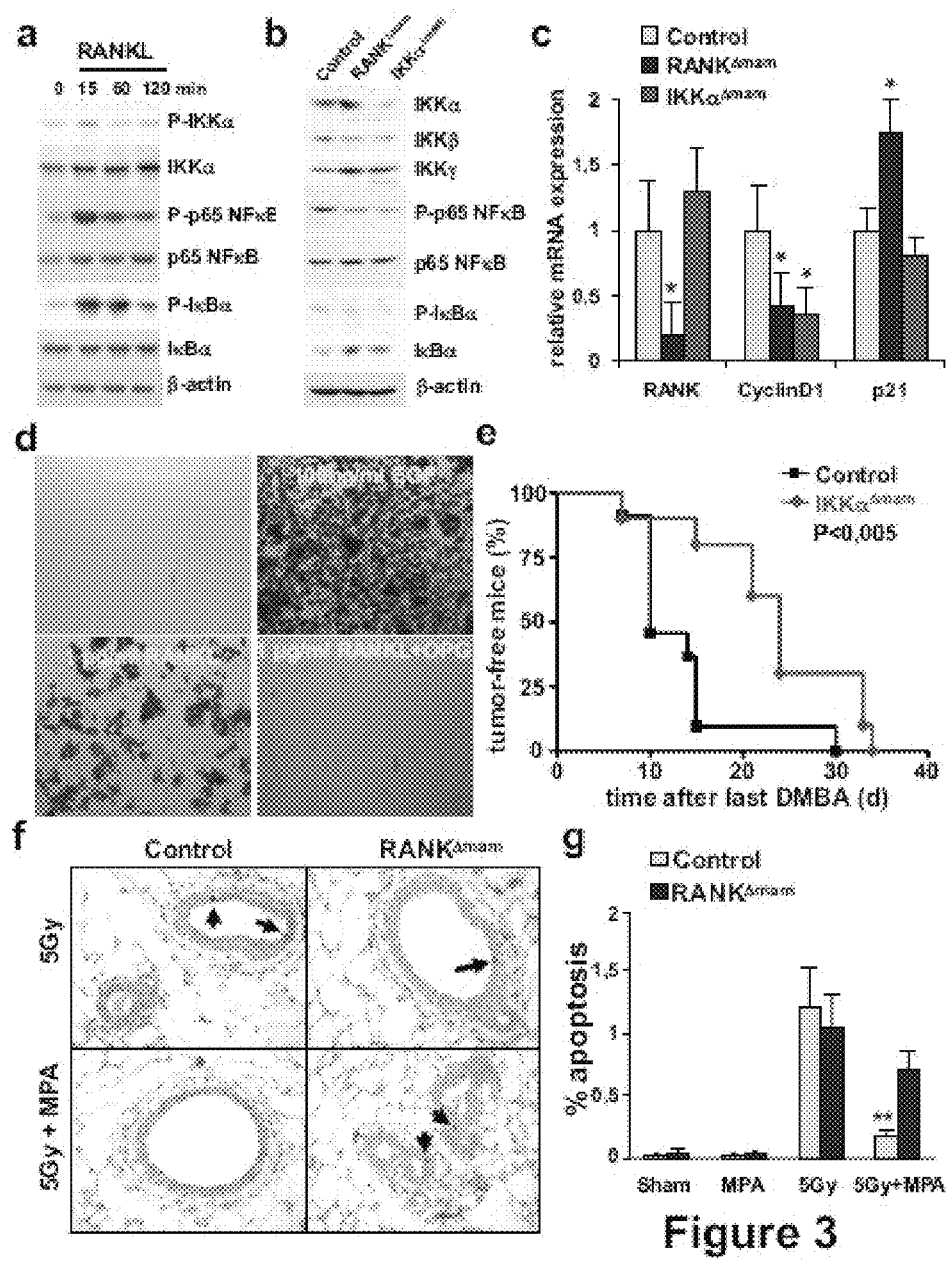

FIG. 3. RANK induces NFκB signaling, anchorage-independent growth, and protects from radiation-induced epithelial apoptosis.

a, Western blotting for phosphorylated (P) IKKα, total IKKα, phosphorylated (P) p65 NFκB, total p65 NFκB, phosphorylated (P) IκBα, and total IκBα in isolated primary mouse mammary gland epithelial cells (MECs) in response to RANKL stimulation (1 μg/ml). β-actin is shown as loading control. b, Western blotting for IKKα, IKKβ, IKKγ, phosphorylated (P) p65 NFκB, total p65 NFκB, phosphorylated (P) IκBα, and total IκBα in pooled late stage mammary adenocarconimas (n=4 for each lane) that developed in control, RANK$^{\Delta mam}$ and IKKΔ$^{\Delta mam}$ females. β-actin is shown as loading control c, Expression of RANK, CyclinD1, and p21 mRNA in late stage mammary adenocacinomas that developed in control, RANK$^{\Delta mam}$, and IKKα$^{\Delta mam}$ females. Expression was determined by qRT-PCR. Data are mean values+/−sem. n=4 per group. d, Soft-Agar Colony Formation Assay. Growth of human SKBR3 breast cancer cells in soft agar in response to stimulation with RANKL (1 μg/ml) or EGF (100 ng/ml). Anchorage-independent, macroscopic colonies formed after 18 days in culture with RANKL, which was prevented by the decoy receptor OPG (1 μg/ml). Controls were unstimulated SKBR3 cells. e, Onset of palpable mammary tumors in IKKα$^{\Delta mam}$ (n=10) and age matched littermate control (n=11) females treated with MPA pellets and DMBA. Data are shown as percentage of tumor free mice after the last DMBA challenge. Median tumor onset for controls was 10 days after last DMBA treatment and 24 days for IKKα$^{\Delta mam}$ females. f,g γ-irradiation (5 Gray) induced mammary epithelial cell apoptosis in control and RANK$^{\Delta mam}$ female littermates either sham operated or implanted with a MPA pellet. Apoptosis was detected by immunostaining for active Caspase 3. f, Apoptotic nuclei of epithelial cells (arrows) are shown for representative mammary gland sections. Magnifications×40. g, Quantification of mammary epithelial apoptosis. A minimum of 5000 nuclei was counted for each mouse. Results shown are mean values+/−sem. n=3 mice per group. *P<0.05; **P<0.02 (Student's t-test).

Figure 4:
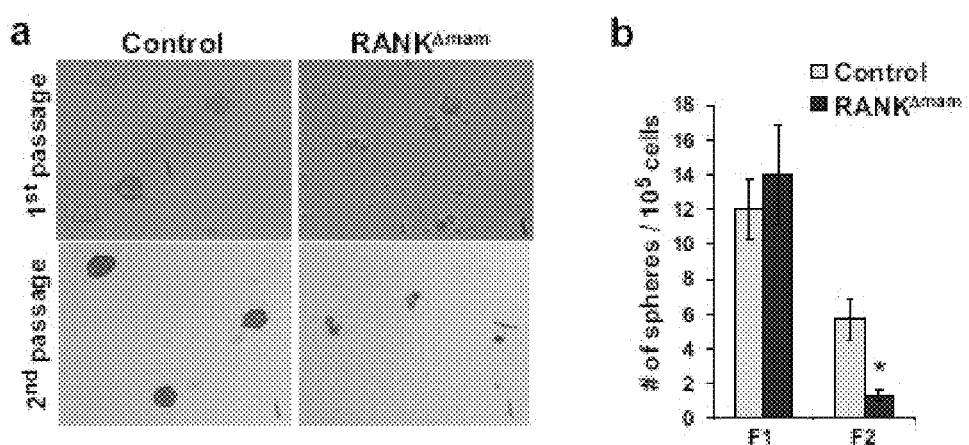

FIG. 4. RANK controls cancer stem cell self renewal a, Self-renewal of mammary cancer stem cells, i.e. tumor initiating cells (TICs) requires RANK expression. Mammary cells from MPA/DMBA-treated RANK$^{\Delta mam}$ and control littermate female were cultured for 7 days and a small percentage of primary cells formed mmospheres (1$^{st}$ passage). Primary mammospheres were then digested into single cells and assayed for their ability to form secondary mammospheres (2$^{nd}$ passage). Tumor cells from control littermate but not from RANK$^{\Delta mam}$ females could form secondary mammospheres determined 7 days after replating. b, Quantification of primary and secondary passage (F1 and F2) mammospheres from MPA/DMBA-treated RANK$^{\Delta mam}$ and control littermate females. Results shown are mean values+/−sem. n=3 mice per group. *P<0.05 (Student's t-test).

Figure 5:
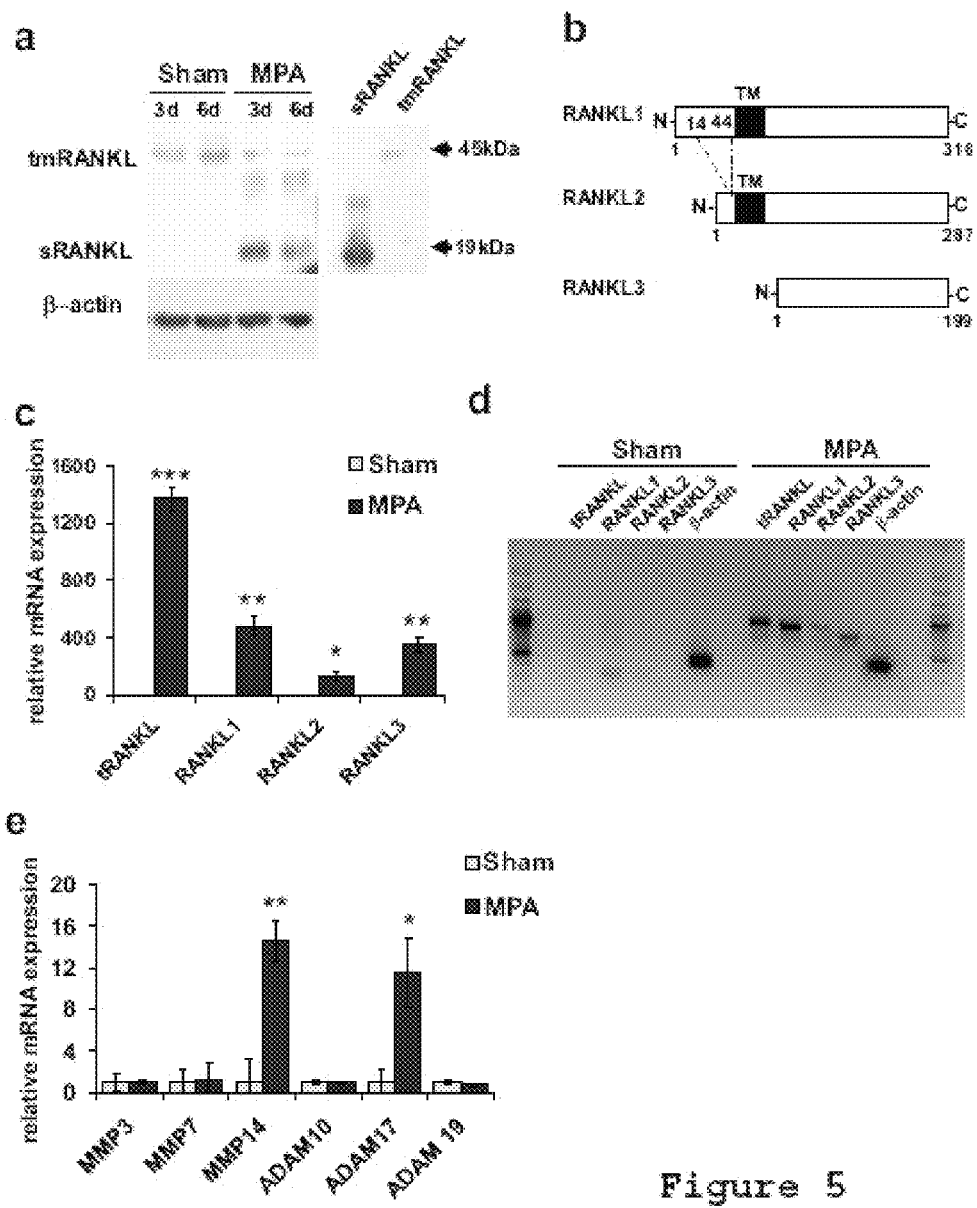

FIG. 5. The progesterone-derivative MPA triggers in vivo RANKL expression.

a-d, Induction of RANKL expression by the progesterone-derivative MPA. Nulliparous wild type females were s.c. implanted with slow-release MPA pellets or treated with surgery sham. a, Expression of transmembrane (tm) and soluble (s) RANKL protein was assayed on isolated mammary gland epithelial cells by Western blot 3 and 6 days after MPA pellet implantation or sham surgery. β-actin is shown as a loading control. Recombinant murine sRANKL and recombinant human tmRANKL protein are shown for molecular size comparison in the right panels. Data are representative of 8 animals tested. b, Schematic representation of the three RANKL isoforms adapted from Ikeda et al. The transmembrane domain of RANKL1 and RANKL2 is indicated (TM, black box, spanning aa 48-71). RANKL2 is lacking as 14-44 of the intracellular domain while RANKL3 is lacking as 1-118 spanning the whole intracellular domain as well as the transmembrane domain. Numbers indicate amino acid residues. c, Expression of total (t) RANKL, RANKL1, RANKL2, and RANKL3 mRNA in purified mammary epithelial cells after three days MPA treatment. β-actin is shown as a control. d, Representative agarose gel of RT-PCR products as in c. e, mRNA expression of various proteases known to shed RANKL from the surface of cells. mRNA was determined in purified mammary epithelial cells by qRT-PCR three days after MPA implantation. Data are shown as fold change compared to sham treatment (+/−sem) (n=3 per group). *P<0.05; P<0.005; *P<0.001 (Student's t-test).

Figure 6:
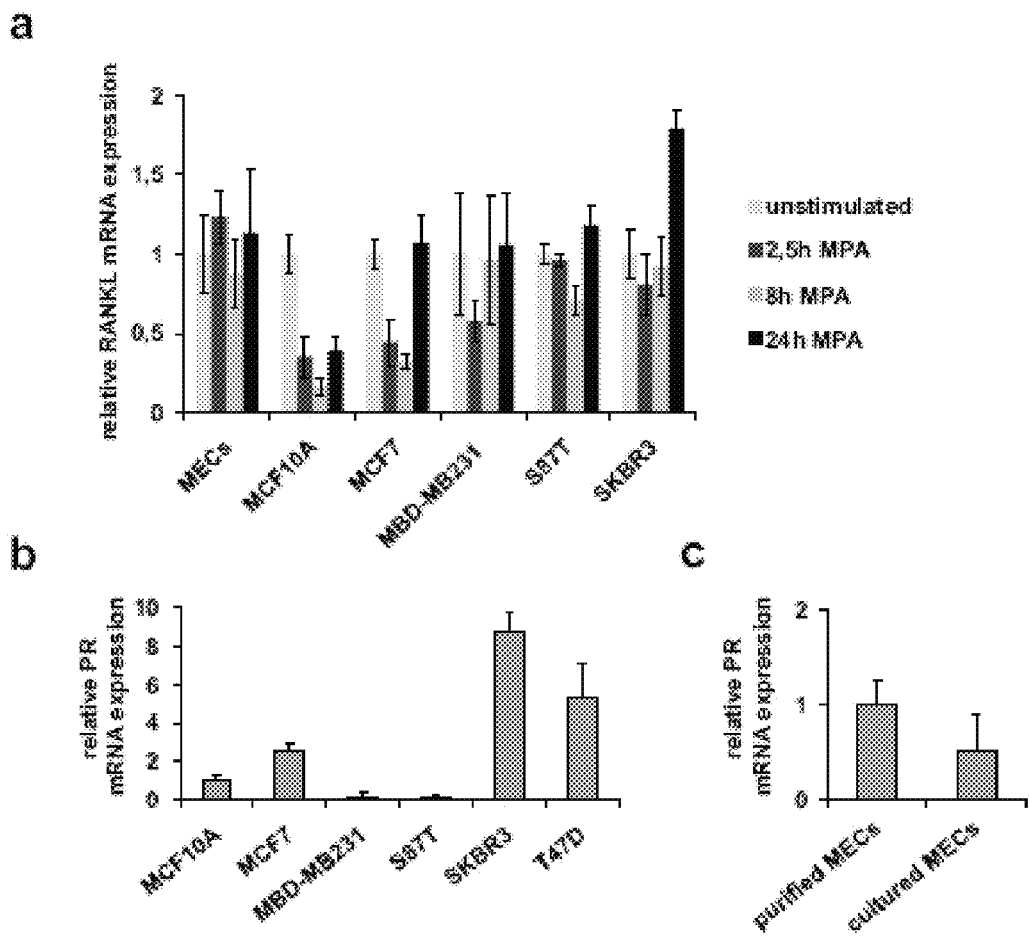

FIG. 6. MPA does not trigger RANKL expression in human breast tumor cell lines.

a, Analysis of RANKL mRNA expression in human breast cancer cells as well as cultured MECs after MPA stimulation (0.1 μM). Expression was determined by qRT-PCR in unstimulated cells or cells stimulated with MPA for the indicated time points. We never fond induction or RANKL with the exception of SKBR3 cells; however, even in these cells induction was only slightly increased as compared to the more than 2000 time increase of RANKL we observed after in vivo MPA challenge. b-c, Progesterone receptor (PR) mRNA was determined in a panel of human breast cancer cell lines (b) and short-term cultured (passage <3) mammary epithelial cells (MECs) and freshly purified primary MECs (c). Data were obtained by qRT-PCR and are shown as fold change compared to MCF10A (b) and purified primary MECs (c) (+/−sem) (n=3).

Figure 7:
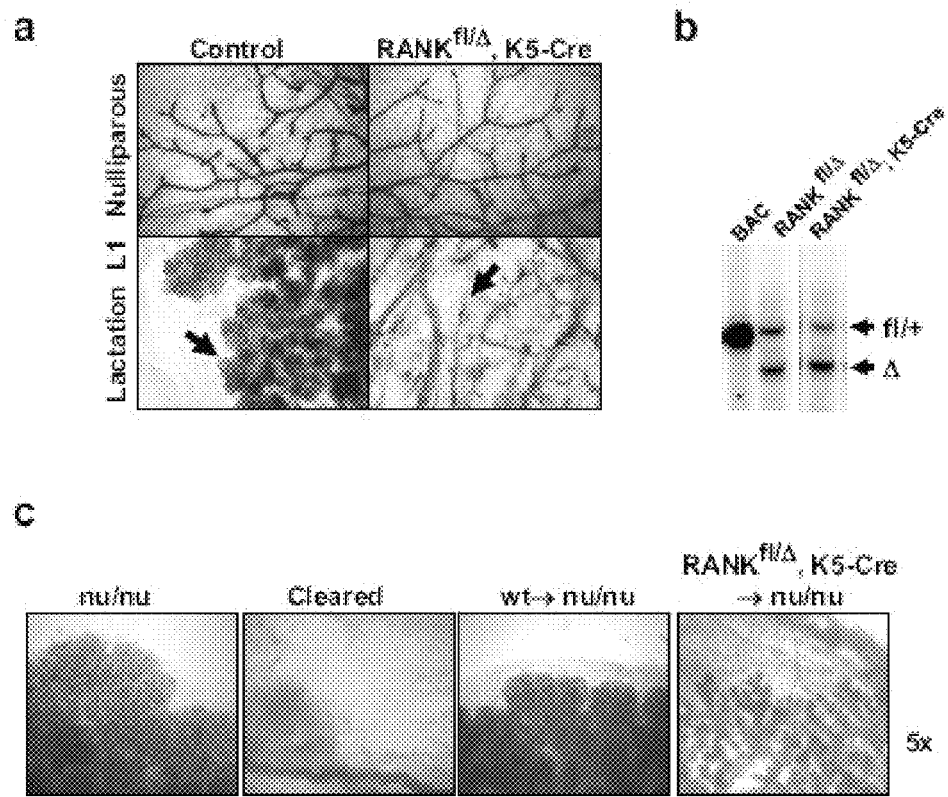

FIG. 7. RANK$^{fl/\Delta}$ females crossed to the K5-Cre mice show defective lobulo-alveolar development in pregnancy.

a, Whole-mount analyses of mammary tissue of nulliparous and lactating (L1) RANK$^{fl/\Delta}$ females crossed with K5-Cre compared to mammary glands of control littermates. Alveoli in gestating wild-type females (arrow) from lobulo-alveolar structures, whereas this development is arrested at a rudimentary alveolar bud (arrow) in K5-Cre RANK$^{fl/\Delta}$ females. b, Southern blot of purified mammary epithelial cells derived from RANK$^{flox/\Delta}$ and RANK$^{flox/\Delta}$; K5-Cre+ females. The wild type or floxed RANK allele (fl/+; 9.6 kb) and the deleted RANK allele (Δ; 3.9 kb) are indicated after digestion of genomic DNA with PvuII and SphI. c, Whole-mount analyses of mammary glands from control BALBc nude (nu/nu) females showing normal lobulo-alveolar structures at day 1 of lactation (L1), normal lobulo-alveolar structures at L1 in "cleared" nu/nu mice transplanted with wild type mammary gland tissue, and defective lobulo-alveolar development at L1 in "cleared" nu/nu mice transplanted with RANK$^{fl/\Delta}$; K5-Cre mammary gland tissue. Fat pads of nu/nu mice after surgical clearing are also shown. All magnifications×5.

Figure 8:
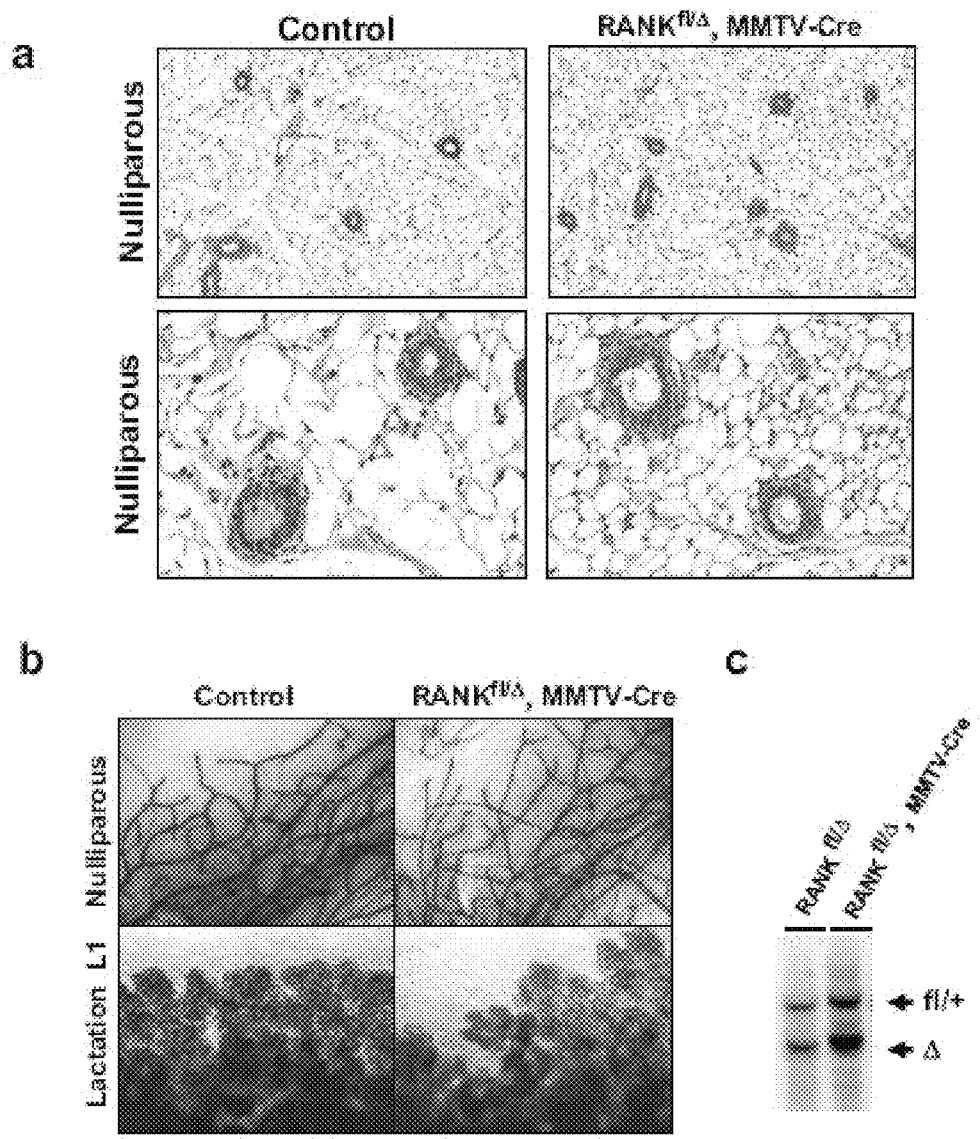

FIG. 8. Normal formation of a lactating mammary gland in pregnant MMTV-Cre, RANK$^{fl/\Delta}$ females.

a, H&E analyses of mammary tissue of nulliparous littermate control and RANK$^{fl/\Delta}$; MMTV-Cre females showing normal alveolar/ductal epithelial structures. Magnifications×10 (top) and ×40 (bottom panels). b, Whole-mount analyses of mammary tissue of nulliparous and lactating (L1) RANK$^{fl/\Delta}$ females crossed with MMTV-Cre compared to mammary glands of control littermates. MMTV-Cre mediated deletion of RANK did not affect formation of a lactating mammary gland. c, Southern blot of purified mammary epithelial cells derived from RANK$^{flox/\Delta}$ and RANK$^{flox/\Delta}$; MMTV-Cre females. The wild type or floxed RANK allele (fl/+; 9.6 kb) and the deleted RANK allele (Δ; 3.9 kb) are indicated after digestion of genomic DNA with PvuII and SphI. RANK$^{flox/\Delta}$; MMTV-Cre animals are denoted RANK$^{\Delta mam}$ hereafter.

Figure 9:
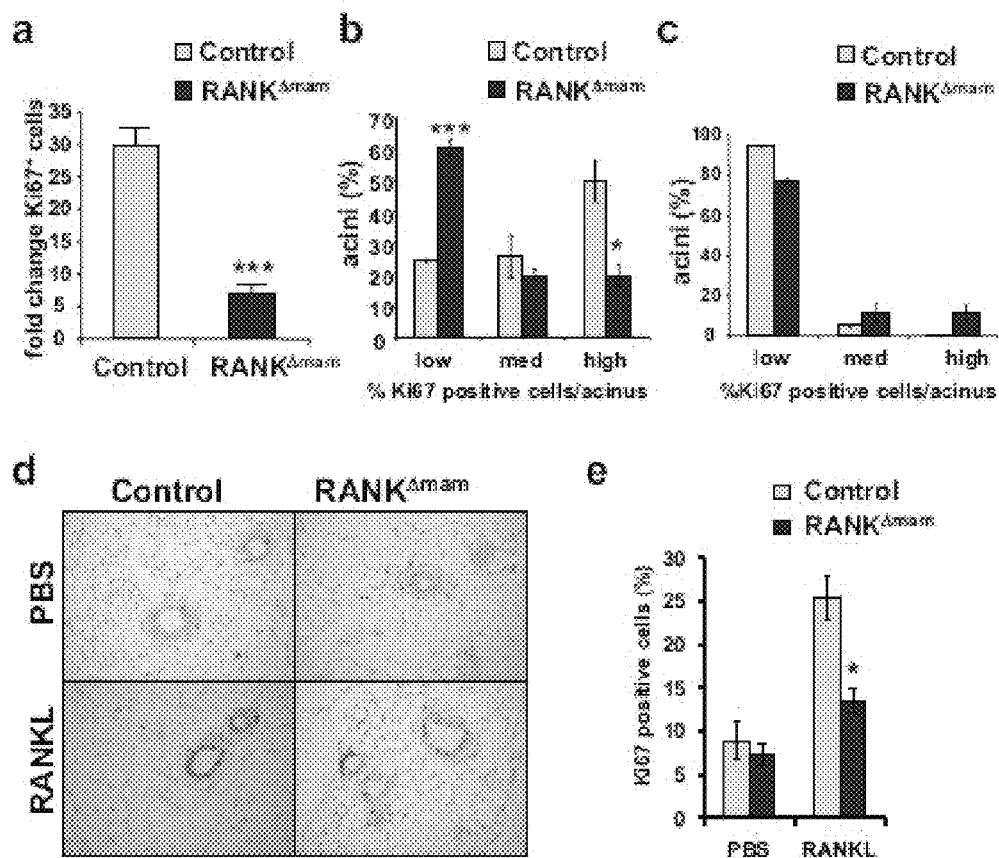

FIG. 9. MPA induces RANKL expression and epithelial proliferation in mammary glands.

a-c, Quantification of epithelial proliferation in mammary glands of control littermates and RANK$^{\Delta mam}$ females 3 days after sham treatment and MPA implantation as shown in FIG. 1d. a, Data are shown as relative changes in total Ki67$^+$ epithelial cells compared to sham-operated females of the respective genotype. At least 1000 mammary gland epithelial cells were counted per mouse. n=3 mice per genotype. P<0.005; *P<0.001 (Student's t-test). b, Quantification of in situ Ki67 immunostained cells per acinus from mammary glands of control littermate and RANK$^{\Delta mam}$ females on day 3 after MPA s.c. implantation. Whereas in control females ~80% of acini showed signs of medium to high proliferation, more than 60% of acini in RANK$^{\Delta mam}$ females exhibited very low proliferation rates. c, To control for estrus-dependent background proliferation levels, superovulated and sham operated control littermate and RANK$^{\Delta mam}$ females were analysed. At least 1000 cells were counted per mammary gland. n=3 per genotype. In b, and c, data are shown as percentage of acini/ducts with low (<20% of epithelial cells are Ki67$^+$), medium (20-80% of epithelial cells are Ki67$^+$) and high (>80% of epithelial cells are Ki67$^+$) numbers of proliferating cells+/−sem. ***P<0.001; *P<0.03 (Student's t-test). d, Epithelial proliferation in mammary glands of control littermates and RANK$^{\Delta mam}$ females 1 day after i.p. injection of PBS or RANKL (1 μg). Proliferation was determined in situ Ki67 immunostaining. Magnifications×40. e, Quantification of epithelial proliferation 1 day after i.p. injection of PBS or RANKL (1 μg). Mean percentages of Ki67 positive cells+/−sem are shown. *P<0.03; n=5 (Student's t-test).

Figure 10:
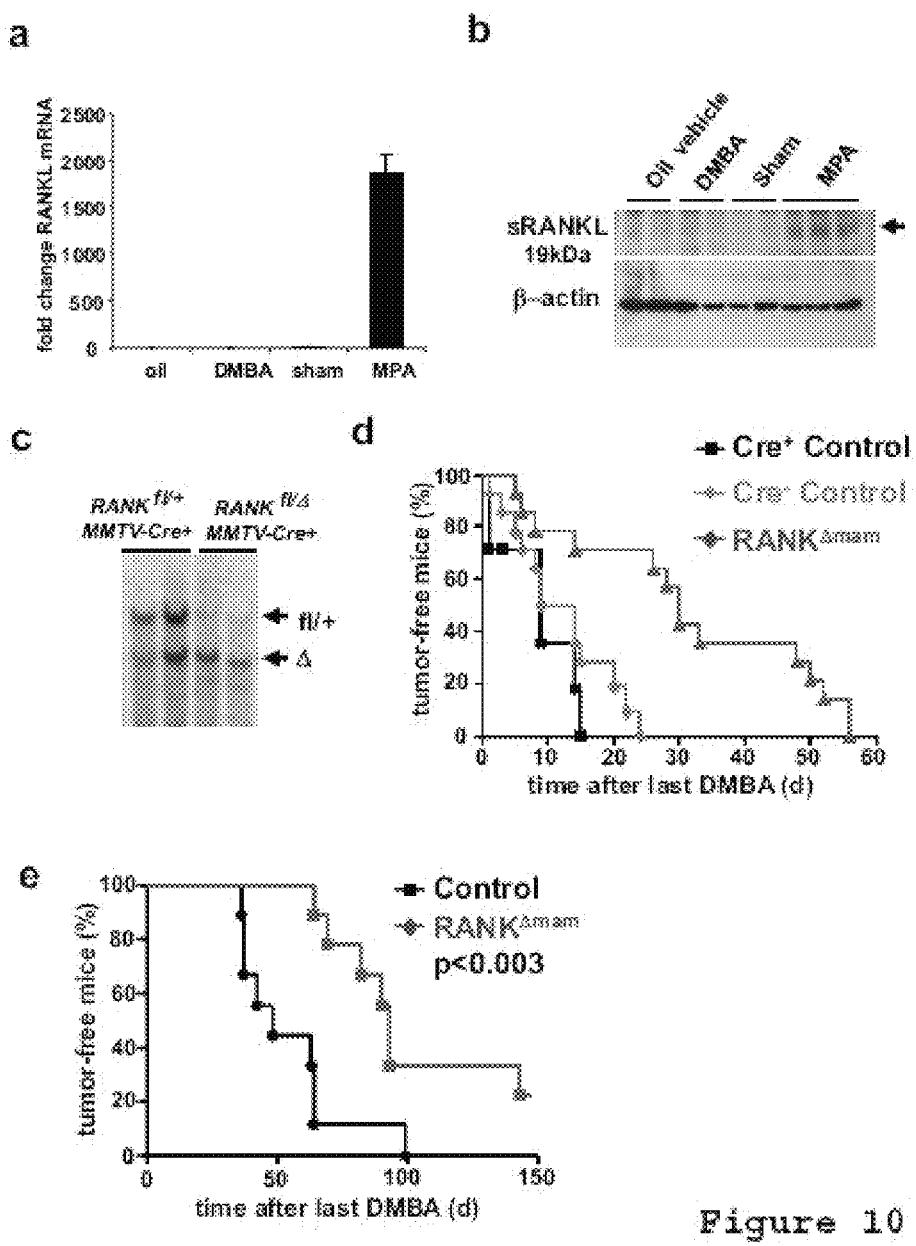

FIG. 10. Survival curves of progestin-driven mammary cancers in RANK$^{\Delta mam}$ mice.

a,b, MPA induces RANKL expression in mammary epithelial cells. Nulliparous wild type females were treated with oral gavage of DMBA or oil vehicle, s.c. implanted with slow-release MPA pellets, or treated with sham surgery. a, RANKL mRNA was determined in purified mammary epithelial cells by qRT-PCR 3 days after implantation/oral gavage. Data are shown as fold change compared to sham treatment+/−sem. n=3 mice per group. b, Expression of soluble (s) RANKL protein (19 kDa) was assayed on cell lysates from purified mammary epithelial cells by Western blot 3 days after treatment with oil vehicle, DMBA, MPA, or sham surgery. β-actin is shown as a loading control. Of note, only MPA but not DMBA or the oil vehicle alone induced RANKL mRNA and protein expression. c, Onset of palpable mammary tumors in RANK$^{\Delta mam}$ (n=14) and age-matched littermate control females with MMTV-Cre (Cre+ control; n=13) or without MMTV-Cre (Cre− control; n=9) treated with MPA pellets and DMBA as indicated in FIG. 2a. Data are shown as percentage of tumor-free mice after the last DMBA challenge. No significant difference was found between the Cre+ and the Cre− control groups. Median tumor onset for Cre+ controls was 9 days, for Cre− controls 11 days, and for RANK$^{\Delta mam}$ females 30 days after the last DMBA treatment. d, Representative Southern blot of MPA/DMBA-induced mammary tumors derived from RANK$^{flox/+}$; MMTV-Cre+ and RANK$^{flox/\Delta}$; MMTV-Cre+ (RANK$^{\Delta mam}$) females. The wild type or floxed RANK allele (fl/+; 9.6 kb) and the deleted RANK allele (Δ; 3.9 kb) are indicated after digestion of genomic DNA with PvuII and SphI. All tumors derived from RANK$^{\Delta mam}$ females showed almost complete deletion. e, Kaplan Mayer analysis for overall survival of RANK$^{\Delta mam}$ (n=9) and age-matched littermate control females (n=9) after treatment with MPA/DMBA. Median survival was 48 days for control and 93 days after the last DMBA treatment for RANK$^{\Delta mam}$ females.

Figure 11:
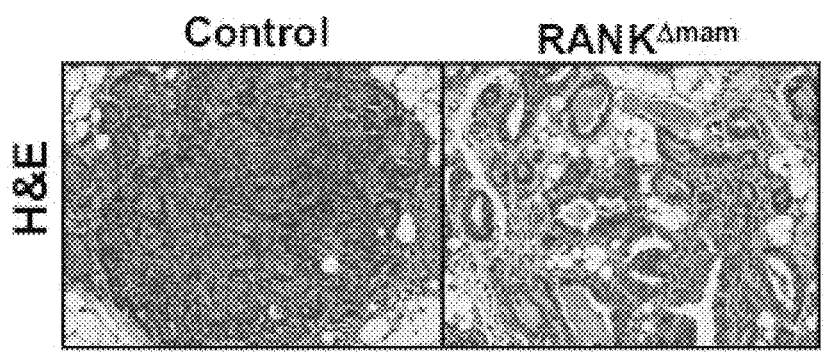
Figure 11:
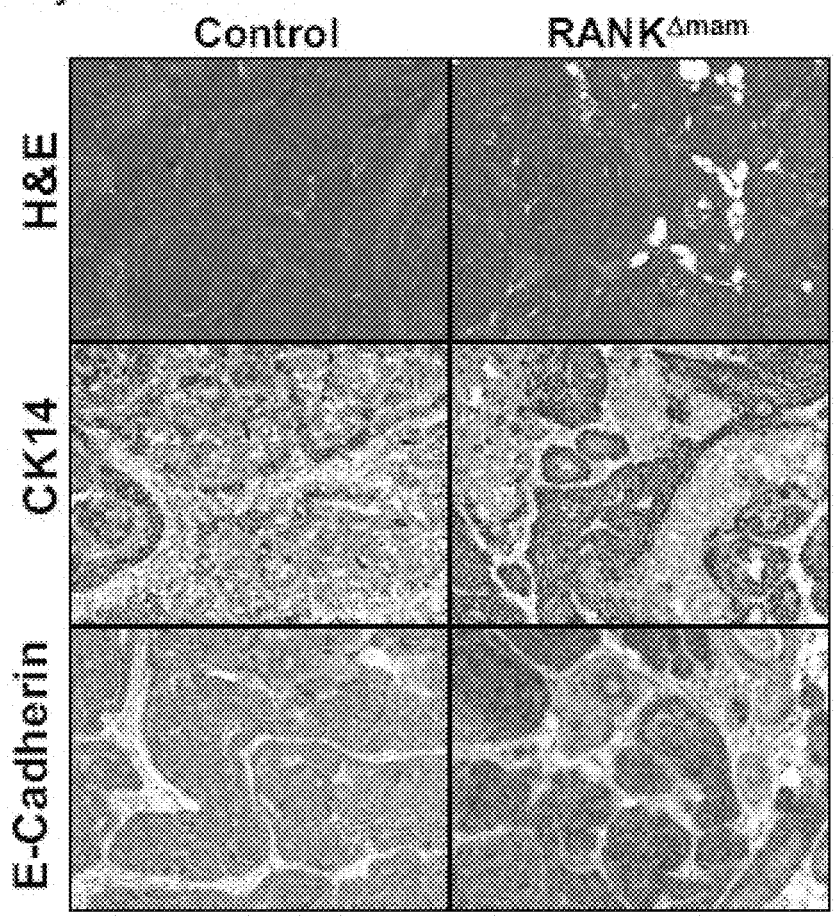

FIG. 11. Development of squamous adenocarcinomas in RANK$^{\Delta mam}$ females.

a,b, Representative histological sections of mammary tumors isolated from control littermate and RANK$^{\Delta mam}$ females 7 (a) and 21 (b) days after the last DMBA treatment. H&E and E-cadherin stainings are shown indicating typical features of ductal adenocarcinomas in tumors from control littermates and RANK$^{\Delta mam}$ females. Cytokeratin14 (K14) expression demonstrates the basal cell origin in both controls and RANK$^{\Delta mam}$ females. However, RANK$^{\Delta mam}$ females tend to show characteristics of squamous metaplasia. All magnifications×20.

Figure 12:
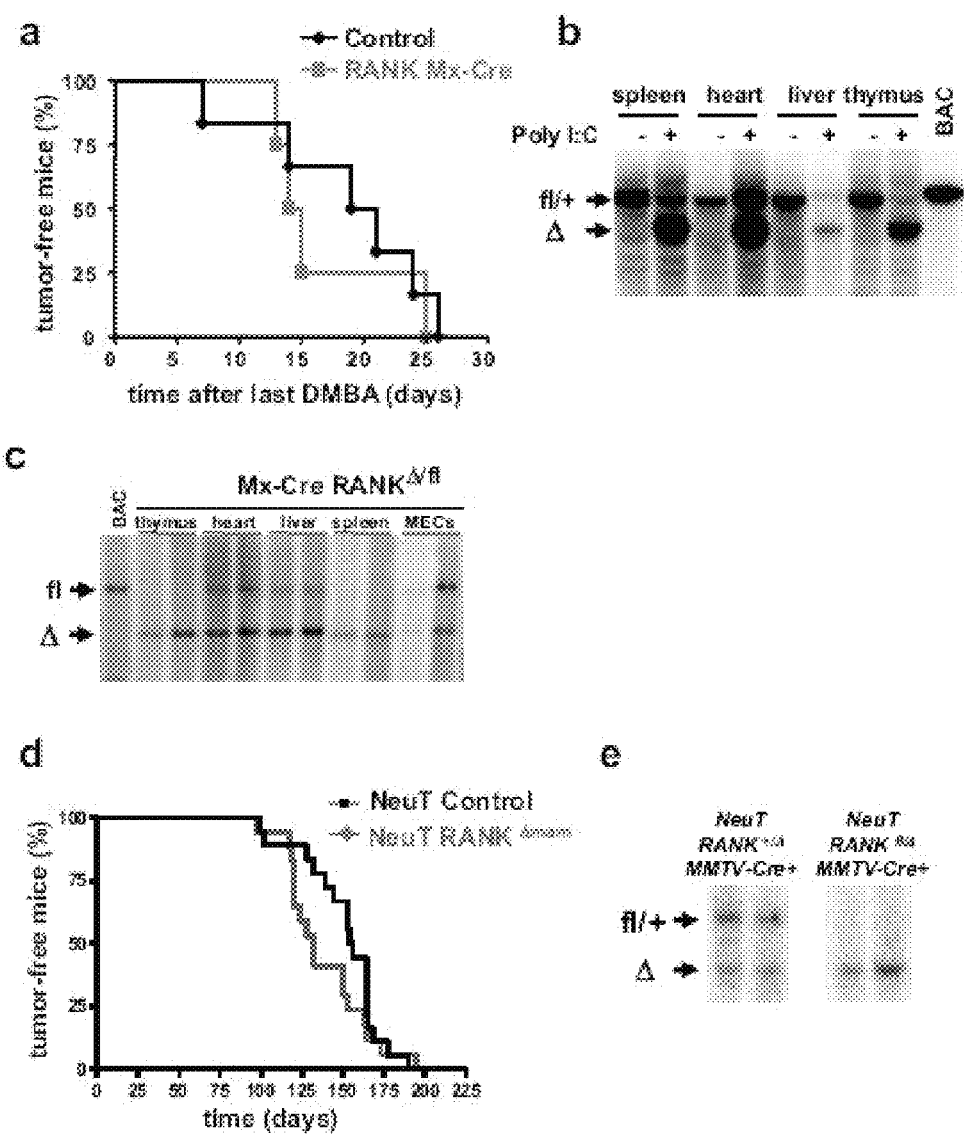

FIG. 12. Mammary cancer onset in Mx-Cre RANK$^{floxed/\Delta}$ and NeuT RANK$^{\Delta mam}$ mice.

a, Onset of palpable mammary tumors in Mx-Cre rank$^{floxed/\Delta}$ (n=4) and age matched Mx-Cre rank$^{+/\Delta}$ littermate control females (n=6) treated with MPA pellets and DMBA as indicated in FIG. 2a. The Mx-driven Cre recombinase was activated by four poly I:C injections i.p. over the course of 8 days (200 μg in 200 ml PBS). Data are shown as percentage of tumor free mice after the last DMBA challenge. No significant differences were found. b, Southern blot of the non-deleted RANK$^{floxed}$ allele (fl/+) and after induction of deletion (Δ) in Mx-Cre rank$^{floxed/\Delta}$ mice. c, Southern blot of various organs after induction of deletion (Δ) in Mx-Cre rank$^{floxed/\Delta}$ mice. While various degrees of deletion (50-100%) can be seen in thymus, heart, liver, and spleen, deletion of the RANK$^{floxed}$ allele was not induced in purified mammary epithelial cells (MECs). d, Onset of palpable mammary tumors in NeuT RANK$^{\Delta mam}$ (NeuT, MMTV-Cre+ rank$^{floxed/\Delta}$) females (n=18) and age matched NeuT (NeuT MMTV-Cre+ rank$^{+/\Delta}$) control littermate females (n=17). No significant difference was found. e, Southern blot of tumors derived from NeuT MMTVCre+ rank$^{floxed/\Delta}$ and mammary cancers from littermate NeuT MMTVCre+ RANK$^{+/\Delta}$ females to control for RANK deletion in tumors.

Figure 13:
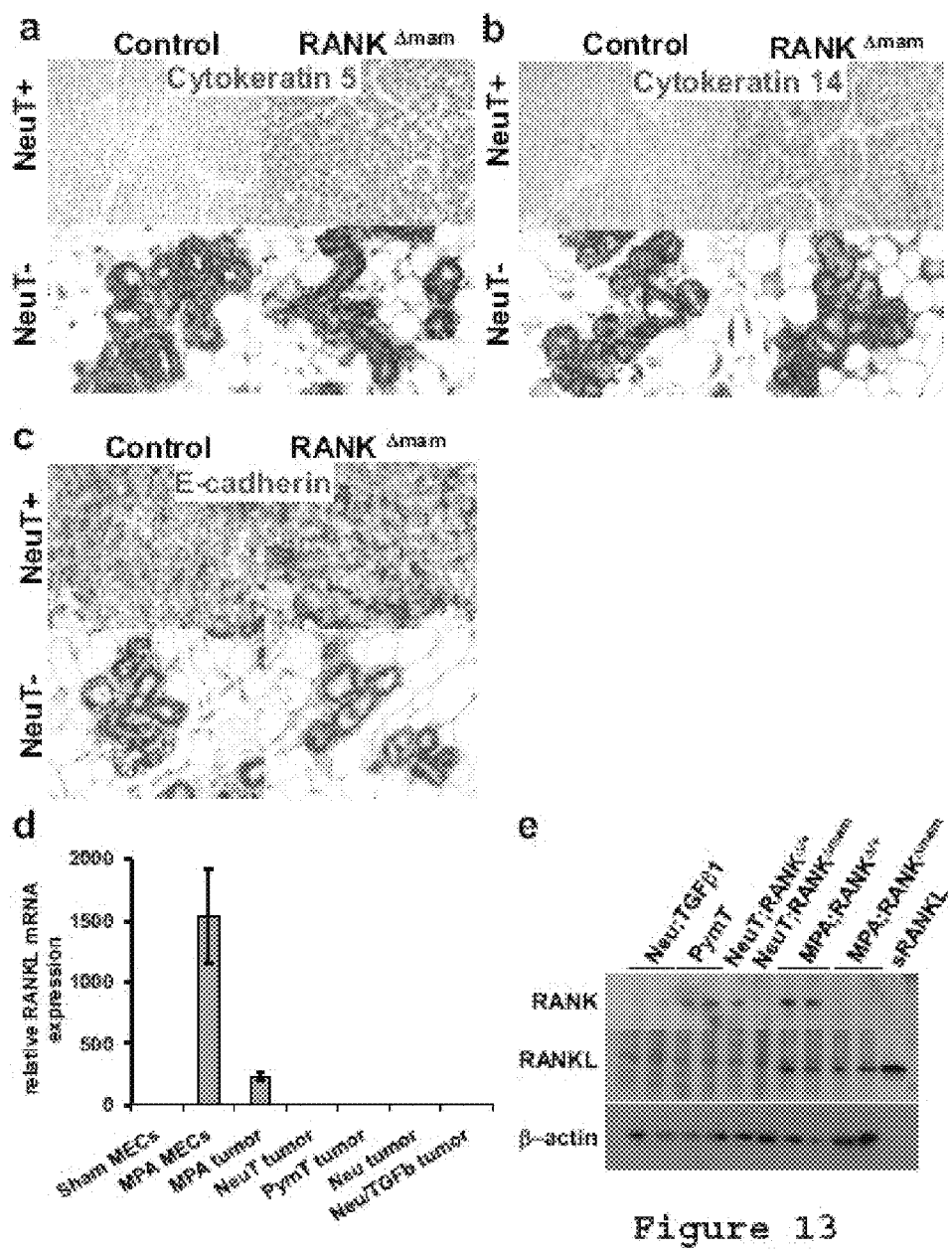

FIG. 13. Tumor formation in NeuT RANK$^{\Delta mam}$ females.

a-c, Representative histological sections with typical adenocarcinomas detected in control and NeuT RANK$^{\Delta mam}$ female mice. Cytokeratin5 (a), Cytokeratin14 (b) and E-cadherin (c) stainings are shown in mammary glands of 6 month-old females. Mammary glands from littermate RANK$^{\Delta mam}$ females not expressing NeuT (NeuT−) are shown as controls. d, RANKL mRNA expression in mammary epithelial cells (MECs) isolated from either sham- or MPA-treated virgin mice, in MPA-driven mamamry adenocarcinomas, and mammary tumors derived from NeuT, Pym, Neu, and Neu/TGFβ transgenic mice. RANKL mRNA was determined by qRT-PCR. Data are shown as fold change compared to sham treatment (+/−sem). n=3 per group. e, RANKL protein expression in various tumors isolated from the indicated genetic mouse models and MPA-driven tumors in control RANK$^{\Delta/+}$ and RANK$^{\Delta mam}$ females. Recombinant murine sRANKL protein is shown for molecular size comparison. β-actin is shown as a loading control.

Figure 14:
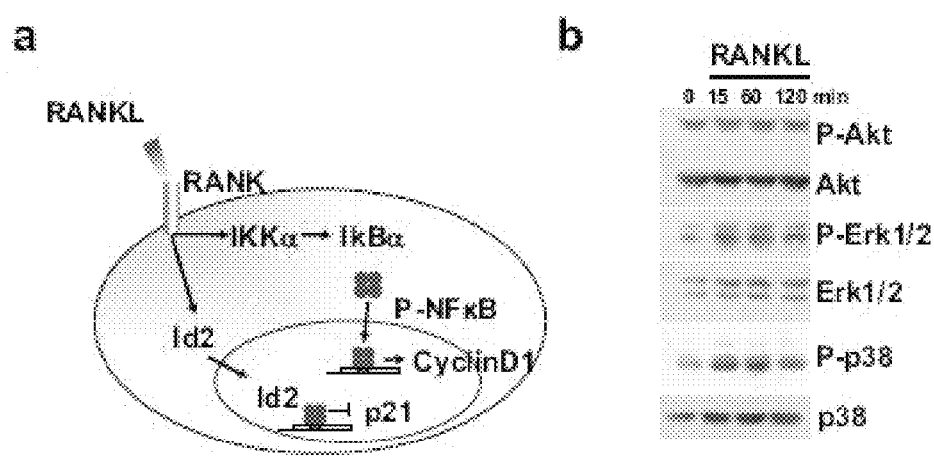

FIG. 14. RANKL/RANK downstream signaling in MECs.

a, Schematic outline of genetically confirmed signalling pathways that control RANKL-RANK mediated formation of a lactating mammary gland during pregnancy. b, Western blotting for phosphorylated (P) AKT, total AKT, phosphorylated (P) ERK1/2, total ERK1/2, phosphorylated (P) p38-MAPK, and p38-MAPK in isolated primary mouse mammary gland epithelial cells in response to RANKL stimulation (1 μg/ml). Data are representative of 4 experiments.

Figure 15:
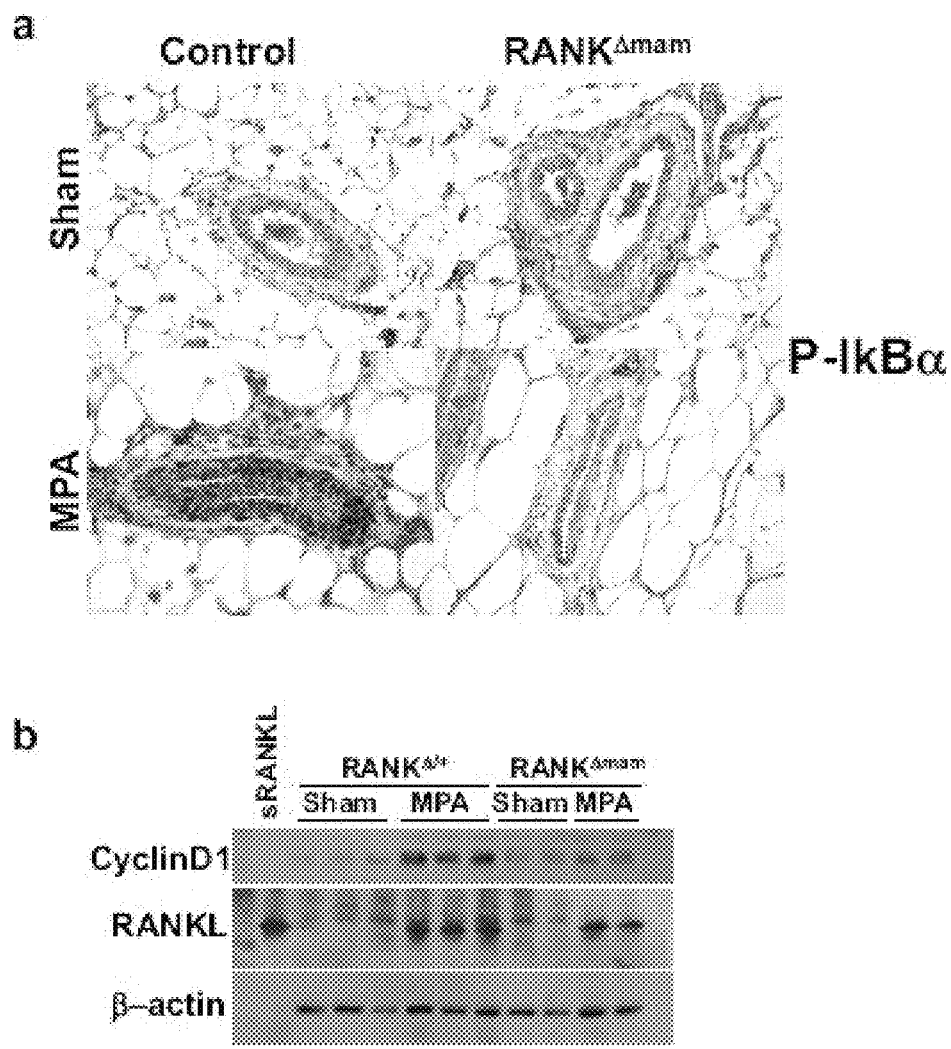

FIG. 15. MPA activates the NFκB pathway and triggers CyclinD1 expression via RANKL/RANK.

a, Activation of the NFκB pathway and CyclinD1 expression by MPA. Nulliparous RANK$^{\Delta mam}$ and littermate control females were s.c. implanted with slow-release MPA pellets or treated with sham surgery. a, In situ immunostaining to detect phosphorylated (P) IκBα in mammary epithelial cells of RANK$^{\Delta mam}$ and littermate control females after 3 d MPA treatment. b, Western blot analysis of CyclinD1 and RANKL in isolated mammary epithelial cells from RANK$^{\Delta mam}$ and littermate control females after 3 d MPA treatment. Recombinant, murine sRANKL protein is shown for molecular size comparison. β-actin is shown as a loading control.

Figure 16:
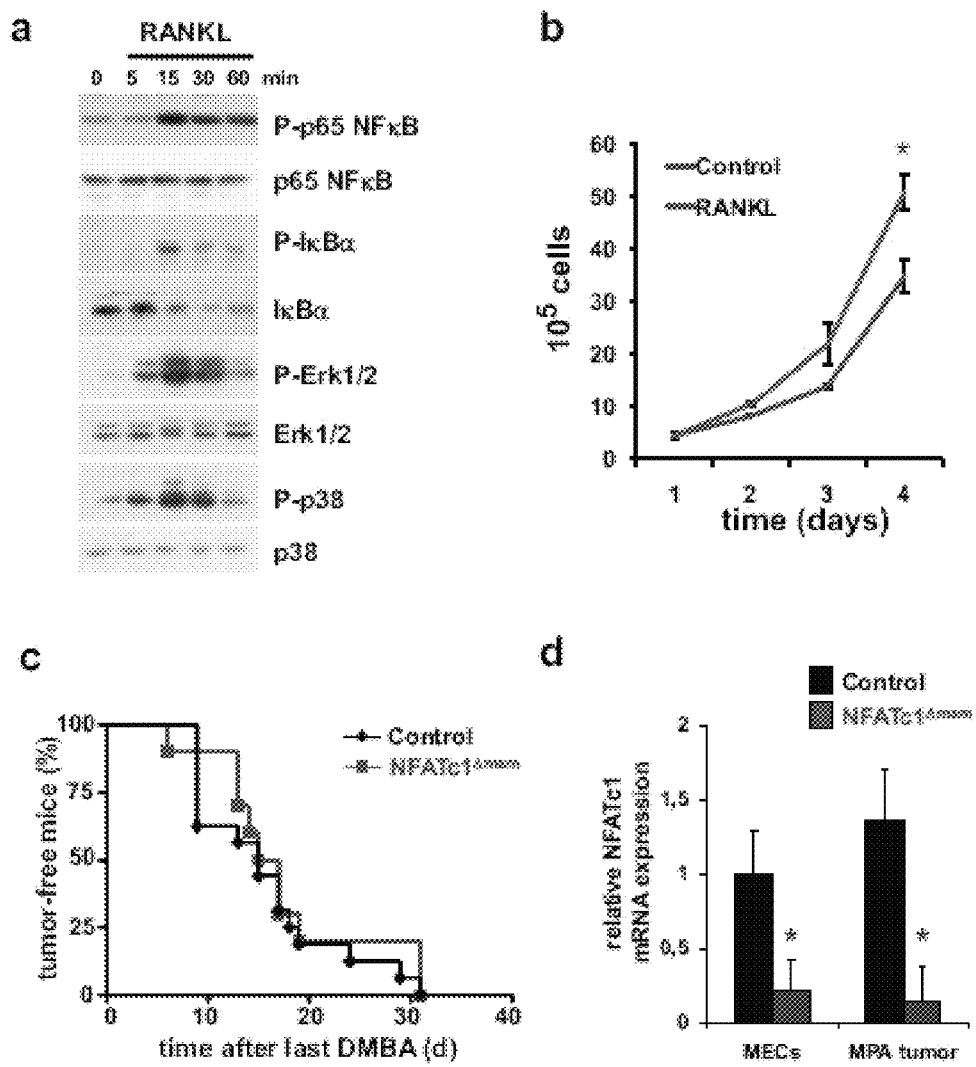

FIG. 16. RANKL/RANK downstream signaling pathways.

a, Western blotting for phosphorylated (P) p65 NFκB, total p65 NFκB, phosphorylated (P) IκBα, total IκBα, phosphorylated (P) ERK1/2, total ERK1/2, phosphorylated (P) p38-MAPK, and p38-MAPK in human SKBR3 breast cancer cells in response to RANKL stimulation (1 μg/ml). Data are representative of 3 experiments. b, Growth curve of SKBR3 breast cancer cells cultured in normal growth medium (control, DMEM supplemented with 10% FCS) or in the presence of RANKL (1 μg/ml). Cell numbers were determined by counting live cells (trypan blue-exclusion) over 3 days. c, Onset of palpable mammary tumors in NFATc1$^{\Delta mam}$ (n=10) and age matched littermate control (n=16) females treated with MPA pellets and DMBA. Data are shown as percentage of tumor free mice after the last DMBA challenge. No significant difference was found. d, Quantification of NFATc1 mRNA expression in purified mammary epithelial cells (MECs) and MPA-driven mammary tumors from NFATc1$^{\Delta mam}$ and littermate control females. mRNA was determined by qRT-PCR. Data are shown as fold change compared to control (+/−sem). n=5 Per group. *P<0.05 (Student's t-test).

Figure 17:
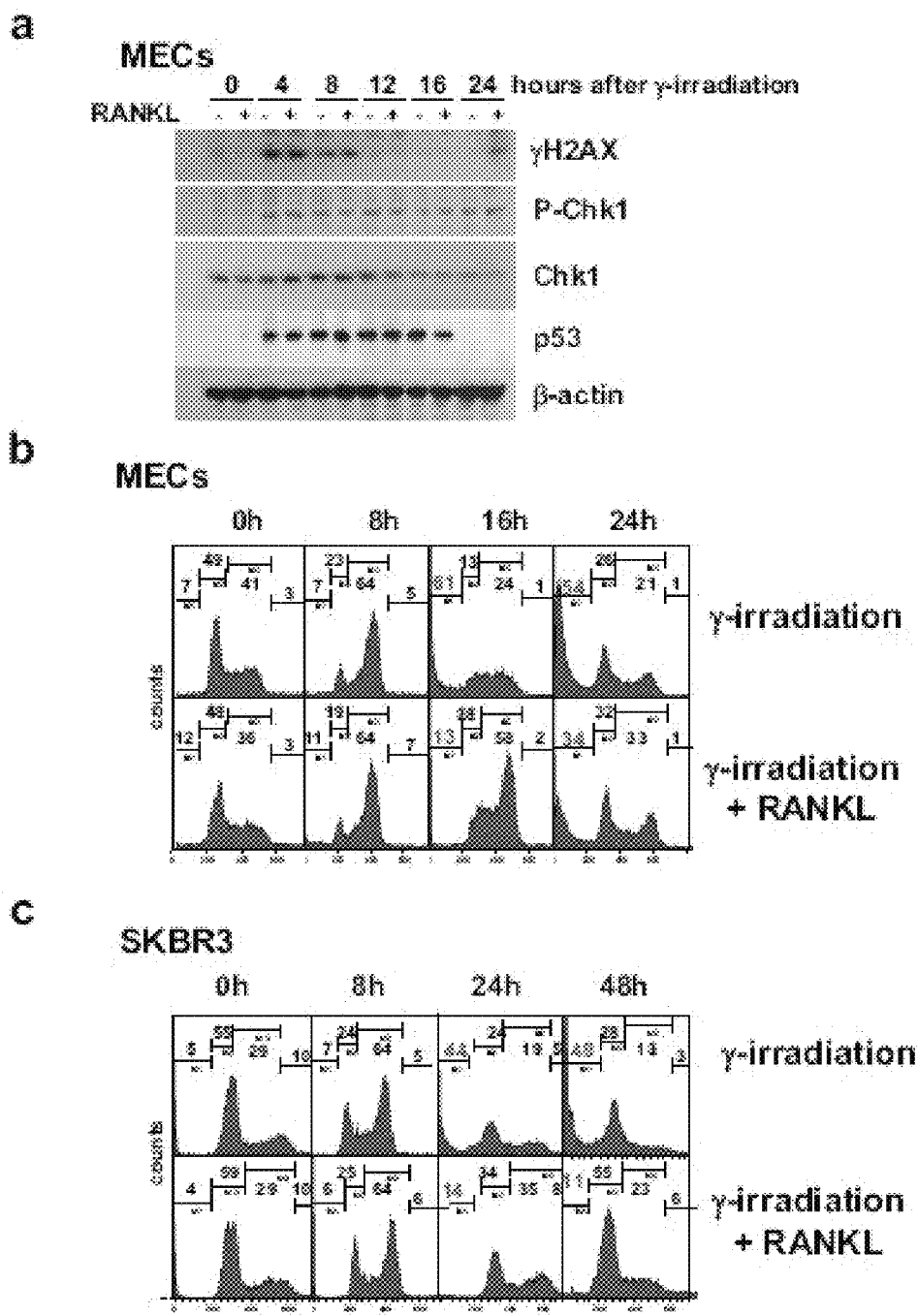

FIG. 17. RANKL protects primary murine mammary epithelial cells and human SKBR3 breast cancer cells from apoptosis in response to γ-irradiation.

a, Western Blot analysis for γH2AX, phosphorylated (P) Chk1, total Chk1, p53 and β-actin in isolated primary mouse mammary gland epithelial cells in response to γ-irradiation (2 Gray) in the presence (1 μg/ml) or absence of RANKL stimulation. b,c, FACS analysis of propidium iodide (PI) stained b, mammary epithelial cells and c, SKBR3 human breast cancer cells after γ-irradiation (2 Gray) in the absence or presence (1 μg/ml) of RANKL. Data are representative of at least 3 experiments. Apoptotic cells with a DNA content <2n appear in the sub-G1 region. Percent of cells in sub-G1 (M1), G1-phase (M2), S/G2/M-phase (M3) as well as polyploid cells with a DNA content >4n are given for the indicated time points.

Figure 18:
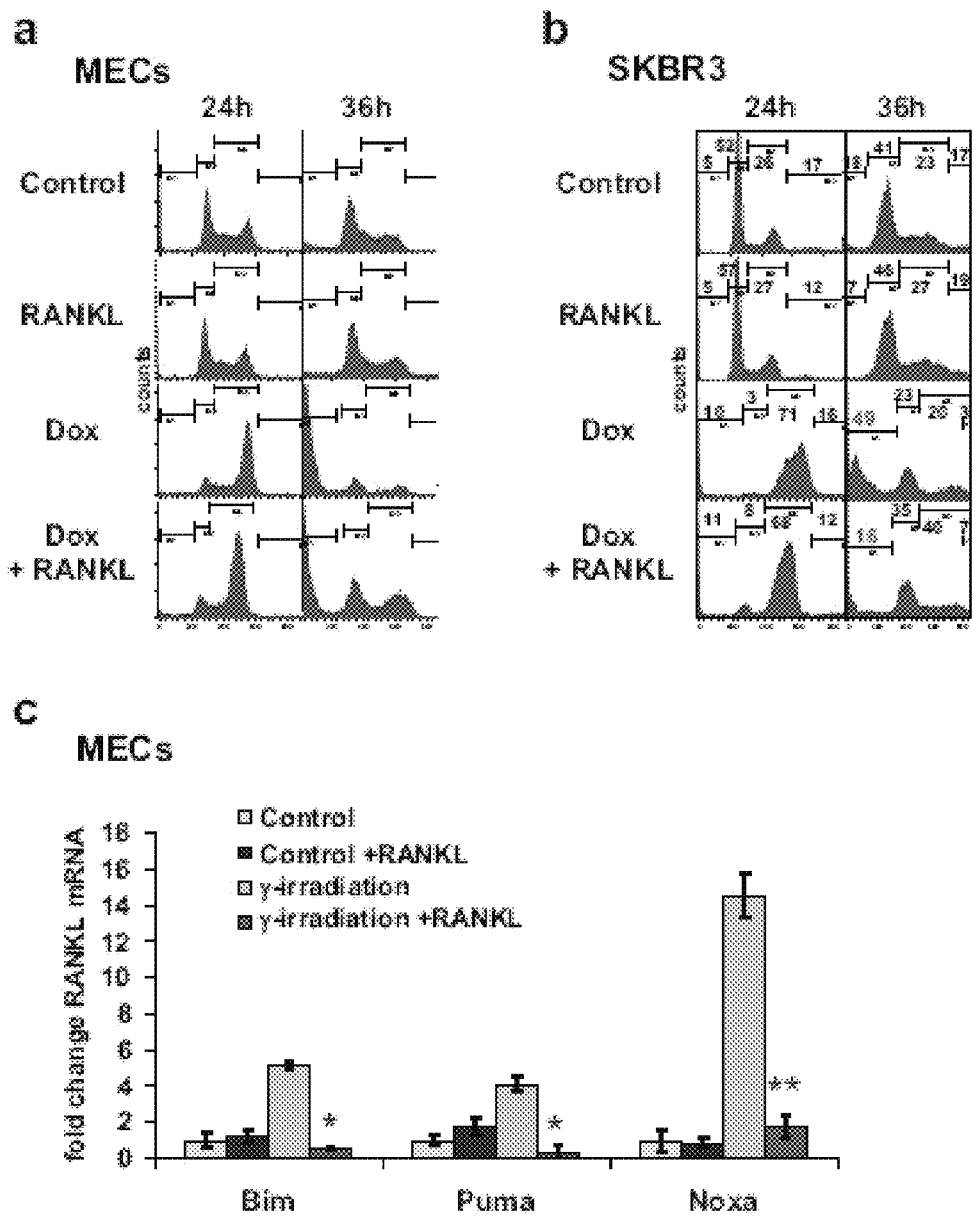

FIG. 18. RANKL protects primary murine mammary epithelial cells and human SKBR3 breast cancer cells from apoptosis in response to doxorubicin.

a,b, FACS analysis of a, mammary epithelial cells and b, SKBR3 human breast cancer cells incubated with the genotoxic agent doxorubicin (Dox, 1 μM) in the presence (1 μg/ml) or absence of RANKL. Data are representative of at least 3 experiments. Percent of cells in sub-G1 (M1), G1-phase (M2), S/G2/M-phase (M3) as well as polyploid cells with a DNA content >4n are given for 24 and 36 hours after doxorubicin treatment. c, mRNA expression of pro-apoptotic genes Bim, Puma, and Noxa 6 hours after γ-irradiation (2 Gray) in the presence (1 μg/ml) or absence of RANKL stimulation. Data are shown as fold change compared to control (+/−sem). n=3). *P<0.05; **P<0.005 (Student's t-test).

Figure 19:
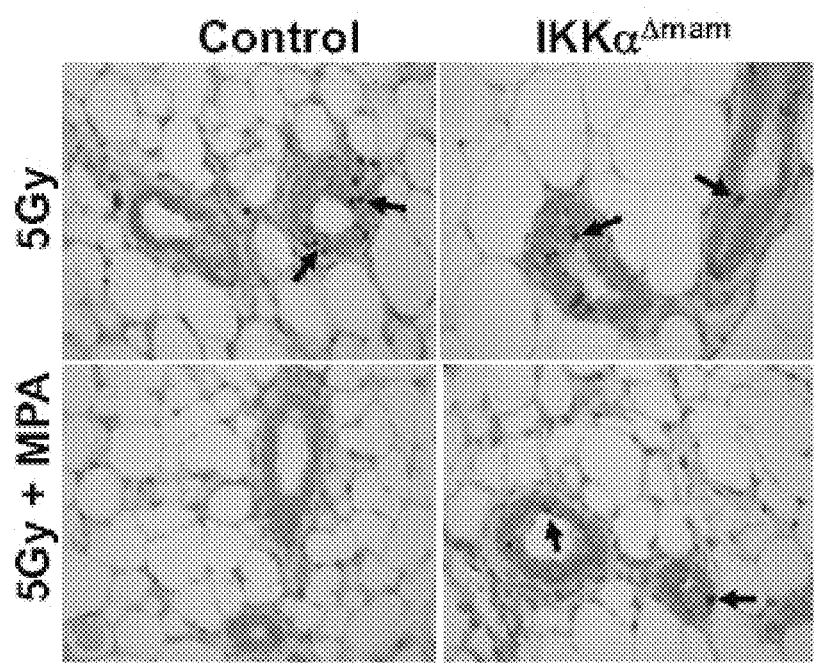
Figure 19:
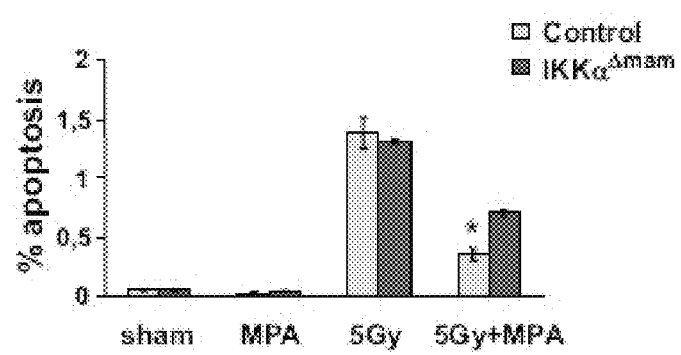

FIG. 19. IKKα mediates MPA-induced protection from radiation-induced epithelial apoptosis.

a,b, Reduced induction of mammary epithelial cell apoptosis in response to γ-irradiation in IKKα$^{\Delta mam}$ females. Littermates control and IKKα$^{\Delta mam}$ females were either sham operated or implanted with an MPA pellet and γ-irradiated (5 Gray). MPA pellets were implanted 3 days before γ-irradiation. 24 hours after irradiation, apoptosis was detected by immunostaining for active Caspase 3. a, Apoptotic nuclei of epithelial cells (arrows) are shown for representative mammary gland sections. Magnifications °40. b, Quantification of mammary epithelial apoptosis. A minimum of 5000 nuclei was counted for each mouse. Results shown are mean values+/−sem. n=3 mice per group. *P<0.05 (Student's t-test).

FIG. 20. Quantification of Western blots.

Densitometry was performed on at least three independent Western blots per experiment. Data are shown for Western blots in FIG. 1b, FIG. 1c, FIG. 3a, and FIG. 3b. Expression values for the indicated proteins were normalized to β-actin loading controls. For quantification of phosphorylation data were normalized to the respective total protein bands. *P<0.05; **P<0.001 (Student's t-test).

EXAMPLES

Example 1

Mice.

Rank$^{floxed}$ mice have been recently generated[1]. Briefly, to generate mice carrying a null allele of Rank (rank$^\Delta$ allele), rank$^{floxed}$ mice were crossed to β-actin-Cre ubiquitous deleter mice. Mice carrying the rank$^{floxed}$ or rank$^\Delta$ alleles as well as the MMTV-Cre mice were backcrossed seven times onto a BALBc background before generating the MMTV-Cre rank$^{\Delta/floxed}$ mice. MMTV-NeuT mice were kindly provided by Guido Forni, Milan. MMTV-Cre (stock #003553) and Mx-Cre mice (stock #003556) were obtained from the Jackson Laboratory. K5-Cre, IKKα$^{floxed}$ and NFATc1$^{floxed}$ mice have been previously described[2-4]. Mouse geno-types were determined by PCR and Southern blot analysis. In all experiments, only littermate mice from the same breedings were used. All mice were bred and maintained according to institutional guidelines.

RANK Deletion in Tumors and Cre Effects.

Southern blotting of the tumors that developed in RANK$^{\Delta mam}$ females showed deletion of RANK, albeit some residual wild type band was observed (FIG. 10c) that may be explained by the presence of other cell types and/or escaper cells. Differences in tumor onset in Cre-negative control females and littermates expressing the MMTV-Cre transgene were not observed indicating that Cre expression per se does not alter tumor incidence in the MPA/DMBA mammary tumor model (FIG. 10d).

Example 2

MPA/DMBA-Induced Mammary Carcinogenesis.

MPA/DMBA treatment was performed as described[5,6]. Briefly, six-week old female mice were anesthetized with ketamine-xylazine and surgically implanted with slow-release Medroxyprogesterone Acetat (MPA) pellets (50 mg, 90-day release; Innovative Research of America) subcutaneously on the right flank. 200 μl DMBA (5 mg/ml diluted in cottonseed oil) was administered by oral gavage 6 times throughout the following 8 weeks as outlined in FIG. 2a. Onset of mammary tumors was determined by palpation. Differences in tumor onset in Cre-negative control females and littermates expressing the MMTV-Cre transgene were not observed indicating that Cre expression per se does not alter tumor incidence in the MPA/DMBA mammary tumor model.

Example 3

Mammary Tissue Transplants.

For transplantation studies, mammary epithelial tissue was isolated from nulliparous 3-week-old donors and implanted into cleared mammary fat pads (devoid of endogenous epithelium) of 3-week-old host nu/nu mice as described[7]. Three weeks after surgery, hosts were mated and mammary tissue was isolated for analysis.

Example 4

Histology, Whole-Mount, and Immunohistochemistry.

For histological analysis, 5 μm sections were cut and stained with hematoxylin and eosin (H&E). Whole-mount staining of mammary glands was performed as described[8]. For immunoperoxidase staining paraffin-embedded sections were dehydrated and antigenic epitopes exposed using a 10 mM citrate buffer or microwaving. Sections were incubated with antibodies to cytokeratine 5, cytokeratine 14, E-cadherin, anti-Ki67 (Novocastra) and anti-active Caspase 3 (Cell Signaling) and visualized using peroxidase-conjugated secondary antibodies. Histomorphometric indices (proliferation and apoptosis) were calculated as the number of positive epithelial cells divided by the total number of epithelial cells, with no fewer than 1000 nuclei for Ki67 stainings and no fewer than 5000 cells for active Caspase 3 staining counted per section.

Example 5

Western Blotting.

The human epithelial breast tumor cell line SKBR3 and primary non-transformed mouse mammary epithelial cells were left untreated or stimulated with recombinant murine RANKL[ref. 9]. Adenocarcinomas were isolated from control and mutant mice and total protein lysates prepared. Western blotting was carried out using standard protocols. Briefly, blots were blocked with 5% BSA in 1×TBS 0.1% Tween-20 (TBST) for 1 hour and incubated with primary antibody overnight at 4° C. (diluted in TBST according to the manufactures protocol). Primary antibodies reactive to mouse RANKL (AF462; R&D), Cyclin D1 (Santa Cruz #Sc-8396), β-actin (Sigma), phosphorylated (P) NFκB (#3033), NF-κB (#4767), phosphorylated (P) IκBα (#2859), IκBα (#4814), phosphorylated (P) IKKα (#2681), IKKα (#2678), IKKβ (#2678), IKKγ (#2685), phosphorylated (P) Akt (#3787), Akt (#9272), phosphorylated (P) Erk1/2 (#9101), Erk1/2 (#9102), and p38-MAPK (#9212), p53 (#2524), phosphorylated (P) Chk1 (#2348), Chk1 (#2345) (all from Cell Signaling), p38-MAPK (AF869; R&D), and γH2Ax (Ser139 #07-164 Millipore) were used. Blots were washed 3 times in TBST for 30 minutes, incubated with HRP-conjugated $2^{nd}$ antibodies (1:2000, Promega) for 1 hour at room temperature, washed 3 times in TBST for 30 minutes, and visualized using ECL.

Example 6 qRT-PCR.

Total RNA of tumors was prepared using the RNeasy Mini Kit (Qiagen), according to the manufacturer's instructions. Total RNA (2 μg) was subjected to quantitative (q)RT-PCR analysis. The following primers were used:
β-actin forward primer: 5'-GCTCATAGCTCTTCTCCA-GGG-3';
β-actin reverse primer: 5'-CCTGAACCCTAAGGC-CAACCG-3'.
RANKL forward primer: 5'-CTGAGGCCCAGCCATTTG-3'
RANKL reverse primer: 5'-GTTGCTTAACGTCATGTTA-GAGATCTTG-3'
RANK forward primer: 5'-CTTGGACACCTGGAAT-GAAG-3'
RANK reverse primer: 5'-CAGCACTCGCAGTCT-GAGTT-3'
CyclinD1 forward primer: 5'-CTGTGCGCCCTCCG-TATCTTA-3'
CyclinD1 reverse primer: 5'-GGCGGCCAGGTTCCACTT-GAG-3'
p21 (Cdkn1a) forward primer: 5'-GTGGCCTTGTCGCT-GTCTT-3'
p21 (Cdkn1a) reverse primer: 5'-GCGCTTGGAGTGATA-GAAATCTG-3'
tRANKL forward primer: 5'-GCGCCGGGCCAGCCGA-GACTAC-3'
RANKL1 forward primer: 5'-GTCCCACACGAGGGTC-CGCTGC-3'
RANKL2 forward primer: 5'-TGCGCACTCCGGCGTC-CCG-3'
RANKL3 forward primer: 5'-CCGAGACTACGGCG-GATCCTAACAG-3'
RANKLcom. reverse primer: 5'-TCAGTCTATGTCCT-GAACTTTGAAAGCCCC-3'
Puma forward primer: 5'-CCGCCTGATGCCCTCCGCTG-TAT-3'
Puma reverse primer: 5'-CGGGCCCACTCCTCCTCCTC-CAC-3'
Noxa forward primer: 5'-ACTTTGTCTCCAATCCTCCG-3'
Noxa reverse primer: 5'-GTGCACCGGACATAACTGTG-3'
Bim forward primer: 5'-GTTGAACTCGTCTCCGATCC-3'
Bim reverse primer 5'-GCCCCTACCTCCCTACAGAC-3'

Example 7

DNA Damage Responses.

For measurement of cell cycle arrest and apoptosis primary mouse mammary epithelial cells and SKBR3 human breast cancer cells were seeded at a cell-density of 100000 cells/well in a 6-well plate and allowed to grow for 24 hours. Cells where then treated with doxorubicin (1 μM) or γ-irradiation (2 Gray) in the absence or presence of recombinant RANKL (1 μg/ml). Cell cycle arrest and numbers of dead cells were determined using propidium iodine staining. To determine in vivo mammary gland epithelial cell death, control and $RANK^{\Delta mam}$ littermate females were γ-irradiated with a total dose of 5 Gray (Gy). Six hours later, mammary glands were isolated and immunostained for active Caspase 3 (Cell Signaling) indicative of apoptosis.

Example 8

FACS Analysis of Primary Mammary Epithelial Cells.

For FACS analysis of mammary epithelial subpopulations the following protocol for tissue dissociation was used to generate single cell suspensions: lymph nodes were removed from both inguinal mammary fat pads and fat pads were then digested in 2 ml complete EpiCult medium (EpiCult-B basal medium (StemCell Technologies SCT Catalog #05610) supplemented with EpiCult-B proliferation supplements, 10 ng/ml bFGF (SCT Catalog #02634), 10 ng/ml EGF (SCT Catalog #02633), 4 μg/ml Heparin (SCT Catalog #07980), 2.5 ml FBS (5%) and antibiotics) with 2.5× colla-genase/hyaluronidase (e.g. 500 μl 10× collagenase+1.5 ml Epicult per mouse) (SCT Catalog #07912) in 50 ml Falcon tubes at 37° C. for 2.5 hours. After vigorous vortexing, pellets were washed with 10 mL HF medium (Hanks Balanced Salt Solution Modified SCT Catalog #07913+2% FBS). Pellets were then resuspended in 2 ml of pre-warmed trypsin-EDTA. After another wash with 10 mL HF, pellets were resuspend in 2 mL pre-warmed (37° C.) dispase (SCT Catalog #07913) supplemented with 200 μl of 1 mg/mL DNAse I (SCT Catalog #07900). After a final wash in HF, cells were counted and prepared for FACS staining. One million cells were incubated with the following antibodies: biotin-conjugated anti-CD31 (#553371; BD), which labels endothelial cells, and biotinylated $CD45^+$ and $Ter119^+$ (StemSep murine chimera cocktail #13058C; Stem Cell Technologies; 3.5 μl/100 μl vol), which labels hematopoietic cells, for 10 min at room temperature. Hematopoietic and endothelial cells were excluded by FACS using Strepavidin-conjugated-APC (#554067; BD). Staining with anti-CD49f (#551129; BD) and CD24 (#553261; BD) was used to identify the mammary stem cell population as previously described[10,11].

Example 9

Cancer Stem Cell Assays.

Self-renewal of mammary cancer stem cells, i.e. tumor initiating cells (TICs), was assayed using a mammosphere assay as described previously[6,12]. Briefly, similar sized tumors (1 cm³ volume) were minced and digested in complete EpiCult medium with 2.5× collagenase/hyaluronidase (SCT Catalog #07912). 2×10⁵ cells were then cultured in serum-free EpiCult medium supplemented with B27 (Invitrogen), 20 ng/ml EGF (Protech), and 20 ng/ml bFGF (Sigma) using 6 well ultra-low attachment plates (Corning Costar). The primary mammospheres, which formed over 7 days, were collected by gentle centrifugation (800 rpm), digested into single cell suspensions with trypsin (0.05%, 10 min), and assayed for their ability to form secondary mammospheres as above.

Example 10

Anchorage-Independent Growth.

The ability of cells to grow in soft agar was assayed as described previously[13]. Briefly, DNA grade agarose (1% in DMEM) was used as bottom layer (2 ml in 6 well plates) and 2×10⁴ SKBR3 cells were seeded in 1.5 ml agarose (0.3% in DMEM). Cells were overlayed with 1.5 ml DMEM supplemented with 10% FCS and cultured for 24 days.

Example 11

Progesterone Assay $1^{st}$ incubation: 30 μL sample—in the presence of a biotinylated monoclonal progesterone-specific antibody and a progesterone derivative labeled with ruthenium complex—are incubated with Danazol to release progesterone. Progesterone from the sample competes with the labeled progesterone derivative for the antibody binding site.

$2^{nd}$ incubation: After addition of streptavidin-coated microparticles, the complex becomes bound to the solid phase via interaction of biotin and streptavidin. The amount of the labeled progesterone derivative bound to the solid phase is inversely proportional to the progesterone content of the sample.

The reaction mixture is aspirated into the measuring cell where the microparticles are magnetically captured onto the surface of the electrode. Unbound substances are then removed with ProCell. Application of a voltage to the electrode then induces chemiluminescent emission which is measured by a photomultiplier.

Results are determined via a calibration curve which is instrument-specifically generated by 2-point calibration and a master curve provided via the reagent barcode.

Reagents—Working Solutions

M Streptavidin-coated microparticles (transparent cap), 1 bottle, 6.5 mL: Streptavidin-coated microparticles, 0.72 mg/mL; preservative.

R1 Anti-progesterone-Ab~biotin (gray cap), 1 bottle, 10 mL: Biotinylated monoclonal anti-progesterone antibody (mouse) 0.15 mg/L, phosphate buffer 25 mmol/L, pH 7.0; preservative.

R2 Progesterone-peptide~Ru(bpy)$_2^{2-}$ (black cap), 1 bottle, 8 mL: Progesterone (of vegetable origin) coupled to a synthetic peptide labeled with ruthenium compley, 10 ng/mL; phosphate buffer 25 mmol/L, pH 7.0; preservative.

Example 12

Statistics.

All values herein are given as means sem. Comparisons between groups were made by Student's t-test. For the Kaplan-Meier analysis of tumor onset a log rank test was performed. P 0.05 was accepted as statistically significant. In addition to the Log RANK test a post-hoc power analysis was performed (PS Power and Sample Size Calculations, in the web at biostat.mc.vanderbilt.edu/PowerSampleSize) to calculate the probability of correctly rejecting the null hypothesis of equal tumor onset times given the number of experimental animals. For the study involving the RANK$^{\Delta mam}$ animals the null hypothesis can be reject with a probability (power) of 0.933 and for the IKKα$^{\Delta mam}$ animals with a probability of 0.766. The Type I error probability associated with this test of this null hypothesis is 0.05. Human data were analysed using a paired t-Test, the Mann Whitney U test, or a Spearman rank test as indicated.

Example 13

Effects of Progestin on RANKL Levels:

MPA (medroxyprogesterone acetate, a representive progestin) pellets were implanted into female mice and RANKL expression was assayed. MPA treatment resulted in a more than 2000 fold induction of RANKL mRNA in isolated mammary epithelial cells (FIG. 1a). mRNA expression of RANK, of the decoy receptor of RANKL osteoprogesterin (OPG), of PTHrP (known to induce RANKL) and of TRAIL (known to bind to OPG) were not changed in isolated mammary epithelial cells. Immunohistochemistry confirmed induction of RANKL protein in the mammary gland (FIG. 1b). Western blotting of isolated mammary epithelial cells also showed induction of the 19 kDa soluble form of RANKL (FIG. 5a), most likely due to alternative splicing (FIG. 5b-d) as well as induction of MMP14 and ADAM17/TACE (FIG. 5e), two proteases known to shed RANKL from the cell surface. RANKL induction in response to MPA in in vitro cell culture assays was not observed (FIG. 6a-c) suggesting that progestins per se are not sufficient to induce RANKL expression. Since MPA can induce transcription of prolactin and the prolactin receptor in breast cancer cells and prolactin can directly induce RANKL via Jak2/Stat5 signaling, it was tested whether MPA induces RANKL in the mammary gland of prolactin receptor knock-out mice. Whereas MPA triggers substantial production of RANKL protein in female control mice, we failed to detect RANKL induction in prolactin receptor mutants (FIG. 1c). This data indicates that MPA triggers massive RANKL expression in the mammary gland via the prolactin receptor and/or that prolactin and MPA cooperate in RANKL induction.

Example 14

Effects of Progestins on RANKL Levels in RANKL/RANK Impaired Mice:

To examine the potential role of RANKL/RANK in MPA-mediated tumorigenesis RANK was deleted in mammary epithelial cells using K5-Cre and MMTV-Cre mediated excision of an inducible RANK allele (K5-Cre rank$^{flox/\Delta}$ mice and MMTV-Cre rank$^{flox/\Delta}$ mice). Both mouse lines appear healthy and exhibit normal bone structures and lymph node formation. As expected K5-Cre rank$^{flox/\Delta}$ mice exhibited apparently normal mammary gland development in puberty; however, these mice did not develop milk-secreting lobuloalveolar structures during pregnancy (FIG. 7a,b). These effects were cell autonomous using transplantation experiments (FIG. 7c). In MMTV-Cre rank$^{flox/\Delta}$ mice, mammary gland development in nulliparous females and formation of milk-secreting lobuloalveolar structures in pregnancy appeared normal (FIG. 8a-c). To exclude any issue of development effects in K5-Cre rank$^{flox/\Delta}$ mice that might affect certain cell populations in normal physiology, MMTV-Cre rank$^{flox/\Delta}$ mice were therefore used for all further experiments. These MMTV-Cre rank$^{flox/\Delta}$ mutant mice are hereafter termed RANK$^{\Delta mam}$.

Example 15

Mechanism of RANKL Activation Upon Progestin Administration:

In a wild type population MPA treatment triggers massive proliferation of mammary epithelial cells. MPA-induced proliferation of mammary epithelial cells was significantly reduced in RANK$^{\Delta mam}$ females (FIG. 1d; FIG. 9a-c). Accordingly, RANKL i.p. injections into nulliparous females triggered proliferation of mammary gland epithelial cells via RANK (FIG. 9d,e). Recently it has been reported that endogenous progesterone affects the numbers of Lin-CD24+CD49f$^{hi}$ stem cells during pregnancy[15] and the estrous cycle[16]. In both studies, the RANKL/RANK system was implicated based on in vivo whole body Ab blocking studies and RT-PCR expression, however, it was not known whether this is a direct effect of RANKL-RANK in mammary epithelial cells rather than a secondary effect. Therefore it was assayed whether progestins such as MPA can also expand Lin-CD24+CD49f$^{hi}$ cells. MPA treatment resulted in a two-fold expansion of Lin-CD24+CD49f$^{hi}$ cells. Such expansion did not occur in MPA-treated RANK$^{\Delta mam}$ females (FIG. 1e,f). These data provide the first genetic proof that the RANKL/RANK system controls expansion of Lin-CD24+CD49f$^{hi}$ cells.

Example 16

Influence of Progestins on Cancer Development Via RANK/RANKL in Control and RANK/RANKL Deficient Mice:

In The Women's Health Initiative (WHI) and the Million Women Study, the use of progestins has been epidemiologically linked to the onset and incidence of breast cancer. Progestin-driven mammary cancer can be modeled in female mice, where implantation of slow release MPA pellets in the presence of the DNA damaging agent dimethylbenz[a]anthracene (DMBA) triggers mammary cancer (FIG. 2a; FIG. 10a,b).

In control females, MPA/DMBA treatment induced a rapid onset of palpable mammary tumors. Intriguingly, in RANK$^{\Delta mam}$ female mice, a marked delay in the onset of MPA/DMBA-induced mammary cancer was observed (FIG. 2b; FIG. 10c,d). Delayed tumor onset on RANK$^{\Delta mam}$ females also resulted in markedly enhanced survival (FIG. 10e). Southern blotting of the tumors that developed in RANK$^{\Delta mam}$ females confirmed efficient deletion of RANK (FIG. 10c). All tumors that developed in control and RANK$^{\Delta mam}$ females exhibited typical histopathology of E-Cadherin expressing ductal adenocarcinomas of the Cytokeratine (CK) 5 and CK14 positive basal cell subtype (FIG. 2c, FIG. 11a,b). However, ductal adenocarcinomas arising in RANK$^{\Delta mam}$ females frequently developed extensive areas of squamous metaplasia (FIG. 2c, FIG. 11a,b). In line with these histopathological changes, gene expression profiling of mammary carcinomas from control and RANK$^{\Delta mam}$ females showed distinctive differences in their molecular signatures as assessed by gene clustering.

Example 17

Cancer Onset after Progestin Challenge and DNA Damage:

Since RANK$^{\Delta mam}$ showed a delayed onset in progestin-induced mammary cancer, next the incidence of mammary tumors at early stages after MPA/DMBA challenge was analysed. One week after the last DMBA treatment, all RANK expressing control females already exhibited multiple in situ carcinomas and even invasive mammary tumors. By contrast, very few carcinomas were observed in situ and never any invasive mammary carcinomas in RANK$^{\Delta mam}$ animals one week after the last DMBA challenge (FIG. 2d). Three weeks after the last DMBA challenge the incidence of carcinomas in situ was similar among control and RANK$^{\Delta mam}$ females, but invasive carcinomas were still very infrequent in the RANK$^{\Delta mam}$ females (FIG. 2e). Moreover, proliferation was typically reduced in tumors from RANK$^{\Delta mam}$ females (FIG. 2d,e). Deletion of RANK in multiple other tissues including the liver, heart, muscle and the haematopoietic compartment, but not in mammary epithelial cells, using Mx-Cre rank$^{flox/flox}$ mice did not delay the onset of MPA/DMBA-induced mammary cancer (FIG. 12a-c), suggesting that the effects of RANK/RANKL impairment are restricted to mammary epithelial cells. Moreover, mammary gland specific deletion of RANK did not alter mammary cancer incidence (FIG. 12d,e) or the histopathology of adenocarcinomas (FIG. 13a-c) in MMTV-NeuT transgenic mice, a genetic model of mammary cancer. In these NeuT tumors very low levels of RANKL were observed (FIG. 13d,e). Thus, genetic inactivation of RANK in mammary epithelial cells results in a markedly delayed onset and reduced incidence of progestin-driven mammary cancer.

Example 18

RANKL Signaling:

RANKL-RANK signaling via IKKα-NFκB-CyclinD1 in mammary epithelial cells is illustrated in FIG. 14a. RANKL stimulation indeed resulted in p65 NFκB and IκBα phosphorylation in primary mouse mammary gland epithelial cells (MECs) (FIG. 3a). In addition, RANKL stimulation of MECs triggered phosphorylation of p38-MAPKs and ERK (FIG. 14b). To directly show whether RANK mediates NFκB-CyclinD1 activation downstream of progestins in vivo, mice were challenged with MPA. A three day MPA treatment resulted in nuclear accumulation of phosphorylated IκBα, indicative of an active NFκB pathway, and induction of CyclinD1 protein expression in mammary epithelial cells, both of which were severely reduced in RANK$^{\Delta mam}$ female (FIG. 15a,b). Moreover, in MPA/DMBA-induced mammary adenocarcinomas isolated from control and RANK$^{\Delta mam}$ females we found impaired activation of the NFκB pathway (FIG. 3b) and downregulated mRNA expression of Cyclin D1 (FIG. 3c). In these primary tumors also upregulation of p21 mRNA (FIG. 3c) was observed, a gene that is transcriptionally suppressed by the Id2 pathway[17]. The Id2 pathway is a second genetically confirmed downstream pathway for RANKL/RANK in mammary epithelial cells[17]. To extend these findings to human, human SKBR3 breast tumor cells were assayed. RANKL stimulation induced NFκB, p38-MAPKs and ERK activation and proliferation in SKBR3 cells (FIG. 16a,b). To further test the effects of RANKL stimulation the ability of these cells to grow in an anchorage-independent manner was assessed, which correlates well with tumorigenicity in vivo[18]. Importantly, similar to EGFR stimulation, it was observed that RANKL induced growth of SKBR3 cells in soft agar (FIG. 3d), i.e. RANK signaling not only triggers proliferation but also acts as a transforming agent to induce anchorage-independent growth.

In osteoclasts, besides the NFκB pathway, the calcineurin-NFATc1 signaling pathway has been found to be essential for RANKL-RANK mediated osteoclastogenesis. NFATc1 can also be regulated by the Id2 pathway during RANKL-mediated osteoclastogenesis. To assess whether these key RANKL-RANK activation pathways are also operational in MPA/DMBA-induced mammary cancer, MMTV-Cre nfatc1$^{flox/\Delta}$ (NFATc1$^{\Delta mam}$) and MMTV-Cre IKKα$^{flox/flox}$ (IKKα$^{\Delta mam}$) mice were generated to delete NFATc1 and IKKα in mammary epithelial cells. Both mutant mouse strains appear healthy and exhibit no overt defects in any organs assayed. When challenged with MPA/DMBA, IKKα$^{\Delta mam}$ mice exhibited a delayed onset of mammary cancer (FIG. 3e). In tumors from IKKα$^{\Delta mam}$ mice normal expression of IKKβ and IKKγ was found but reduced NFκB activation as determined by increased IκB protein levels and decreased p65 NFκB phosphorylation (FIG. 3b) and downregulated mRNA expression of the NFκB target gene Cyclin D1 (FIG. 3c) suggesting that IKKα is indeed required for NFκB signaling in these tumors. As expected, the Id2 pathway gene p21 was not affected in tumors from IKKα$^{\Delta mam}$ mice (FIG. 3c). No significant differences in the tumor onset between control and NFATc1$^{\Delta mam}$ mice were observed (FIG. 16c,d), suggesting that downstream signaling requirements are different in osteoclast progenitors and mammary gland epithelial cells. Thus, deletion of IKKα, but not NFATc1, in mammary gland epithelial cells affects the onset of progestin-driven mammary cancer.

Example 19

Hormone Driven Cancer Development Due to DNA Damage:

Although MPA treatment induces very rapid and massive proliferation of mammary epithelial cells, MPA alone is not sufficient to trigger mammary cancer which requires a carcinogen to induce DNA mutations. To analyze the role of RANKL in the cellular response to DNA damage such as cell cycle arrest and apoptosis, mouse primary mammary epithelial cells (MECs) and the RANKL-responsive human breast cancer cell line SKBR3 were treated with DNA damaging agents doxorubicin or γ-irradiation. RANKL treatment did not alter induction of γH2AX and p53 or activation of Chk1, prototypic markers of a functional DNA damage response (FIG. 17a). Moreover, RANKL did not alter the early cell cycle arrest after DNA damage with γ-irradiation (FIG. 17b,c) or doxorubicin (FIG. 18a,b). Surprisingly, RANKL treatment resulted in a marked protection from cell death in response to γ-irradiation (FIG. 17b,c) and doxorubicin-induced DNA damage (FIG. 18a,b). Mechanistically, γ-irradiation-induced upregulation of the proapoptotic molecules Bim, Puma, and Noxa did not occur in the presence of RANKL (FIG. 18c). In vivo it has been shown that γ-irradiation of female mice results in a 5-fold induction of apoptosis of mammary epithelial cells[19]. Therefore this previously established system was used to assess the effects of the MPA-RANKL/RANK axis on γ-irradiation-induced cell death. MPA treatment indeed protected from γ-irradiation-induced apoptosis of mammary epithelial cells in vivo. Loss of RANK expression on mammary epithelial cells abrogated the protective effects of MPA on γ-irradiation-induced cell death (FIG. 3f,g). Moreover, the IKKα pathway was involved in MPA-induced protection of the mammary epithelium after γ-irradiation (FIG. 19a,b). Thus, in addition to promoting cell cycle progression, MPA can protect from cell death after DNA damage via RANKL/RANK and IKKα signaling.

Example 20

Tumor Inhibiting Stem Cells:

Recently it has been shown in humans and mice that mammary tumors might arise from stem cell populations[20]. Therefore it was tested whether loss of RANK affects mammary cancer stem cells, i.e. tumor initiating cells (TICs). TICs can be functionally assayed by their ability to form non-adherent mammospheres[20]. Freshly isolated cancer cells from control and RANK$^{\Delta mam}$ females were able to form primary mammospheres, however, after dispersion into single cells the ability to form secondary mammospheres was significantly impaired using TICs from RANK$^{\Delta mam}$ mice (FIG. 4a,b). These data indicate that loss of RANK activity or expression markedly impairs the self-renewal capacity of cancer stem cells.

Example 21

Discussion:

Based on these results the following molecular mechanism how hormones such as MPA drive cancer via RANKL is apparent: MPA triggers an enormous induction of RANKL in the mammary gland. The induction of RANKL in response to MPA requires expression of the prolactin receptor and possibly other intermediates. RANKL via RANK on mammary epithelial cells drives these cells into the cell cycle and, importantly, protects mouse as well as human mammary gland epithelial cells from apoptosis in response to DNA damage including γ-irradiation. Moreover, RANKL-/RANK control self renewal of mammary cancer stem cells and anchorage-independent growth. Thus, progestin-induced RANKL/RANK provide a growth and survival advantage to damaged mammary epithelium, a prerequisite to initiate mammary cancer[21]. These effects are, at least in part, mediated via the IKKα-NFκB signaling pathway. Millions of women take progesterone-derivatives in contraceptives and for hormonal replacement therapy. Such hormones have been epidemiologically linked to an increased risk to develop breast cancer. The present invention shows that the RANKL-RANK system is an important molecular link between progestins and epithelial carcinogenesis. RANKL inhibition is therefore a novel approach to prevent and/or treat cancer. RANKL inhibition can also be used to prime cancer cells for anti-cancer therapy such as based on radiation or other DNA damaging agents.

REFERENCES

1. Hanada, R. et al. Central control of fever and female body temperature by RANKL/RANK. Nature 462, 505-9 (2009).
2. Tarutani, M. et al. Tissue-specific knockout of the mouse Pig-a gene reveals important roles for GPI-anchored proteins in skin development. Proc Natl Acad Sci USA 94, 7400-5 (1997).
3. Gareus, R. et al. Normal epidermal differentiation but impaired skin-barrier formation upon keratinocyte-restricted IKK1 ablation. Nat Cell Biol 9, 461-9 (2007).

4. Aliprantis, A. O. et al. NFATc1 in mice represses osteoprotegerin during osteoclastogenesis and dissociates systemic osteopenia from inflammation in cherubism. J Clin Invest 118, 3775-89 (2008).
5. Aldaz, C. M., Liao, Q. Y., LaBate, M. & Johnston, D. A. Medroxy-progesterone acetate accelerates the development and increases the incidence of mouse mammary tumors induced by dimethylbenzan-thracene. Carcinogenesis 17, 2069-72 (1996).
6. Cao, Y., Luo, J. L. & Karin, M. IkappaB kinase alpha kinase activity is required for self-renewal of ErbB2/Her2-transformed mammary tumor-initiating cells. Proc Natl Acad Sci USA 104, 15852-7 (2007).
7. Robinson, G. W. & Hennighausen, L. Inhibins and activins regulate mammary epithelial cell differentiation through mesenchymal-epithelial interactions. Development 124, 2701-8 (1997).
8. Fata, J. E. et al. The osteoclast differentiation factor osteoprotegerin-ligand is essential for mammary gland development. Cell 103, 41-50 (2000).
9. Lacey, D. L. et al. Osteoprotegerin ligand is a cytokine that regulates osteoclast differentiation and activation. Cell 93, 165-76 (1998).
10. Stingl, J. et al. Purification and unique properties of mammary epithelial stem cells. Nature 439, 993-7 (2006).
11. Shackleton, M. et al. Generation of a functional mammary gland from a single stem cell. Nature 439, 84-8 (2006).
12. Dontu, G. et al. In vitro propagation and transcriptional profiling of human mammary stem/progenitor cells. Genes Dev 17, 1253-70 (2003).
13. Freedman, V. H. & Shin, S. I. Cellular tumorigenicity in nude mice: correlation with cell growth in semi-solid medium. Cell 3, 355-9 (1974).
14. Jones, D. H. et al. Regulation of cancer cell migration and—bone metastasis by RANKL. Nature 440, 692-6 (2006).
15. Asselin-Labat, M. L. et al. Control of mammary stem cell function by steroid hormone signalling. Nature.
16. Joshi, P. A. et al. Progesterone induces adult mammary stem cell expansion. Nature.
17. Kim, N. S. et al. Receptor activator of NF-kappaB ligand regulates the proliferation of mammary epithelial cells via Id2. Mol Cell Biol 26, 1002-13 (2006).
18. Freedman, V. H. & Shin, S. I. Cellular tumorigenicity in nude mice: correlation with cell growth in semi-solid medium. Cell 3, 355-9 (1974).
19. Ewan, K. B. et al. Transforming growth factor-beta1 mediates cellular response to DNA damage in situ. Cancer Res 62, 5627-31 (2002).
20. Pece, S. et al. Biological and molecular heterogeneity of breast cancers correlates with their cancer stem cell content. Cell 140, 62-73.
21. Hanahan, D. & Weinberg, R. A. The hallmarks of cancer. Cell 100, 57-70 (2000).

The invention claimed is:

1. A method of delaying the onset of a primary breast or mammary cancer in a human patient comprising administering a therapeutically effective amount of anti-RANKL antibody to said patient;
   wherein the patient does not have cancer,
   wherein the patient is a pre-menopausal female at risk of developing the primary breast or mammary cancer, and
   wherein the patient does not show bone loss.

2. The method of claim 1, wherein the patient has received one or more treatments selected from treatment with a female sexual hormone, hormone replacement therapy and treatment with a hormone contraceptive.

3. The method of claim 1, wherein the anti-RANKL antibody is administered in combination with a therapy of female sexual hormones.

4. The method of claim 1, wherein the anti-RANKL antibody is administered in a pharmaceutical composition together with a hormone or derivative thereof selected from estrogen, progesterone, a progestin and a hormone contraceptive.

5. The method of claim 4, wherein the composition further comprises a pharmaceutically acceptable diluent, carrier, solubilizer, emulsifier, preservative and/or adjuvant.

6. The method of claim 1, wherein the anti-RANKL antibody is administered together with a chemotherapeutic agent for prevention of breast or mammary cancer.

7. The method of claim 1, wherein the primary breast or mammary cancer does not overexpress HER2/neu.

8. The method of claim 1, wherein said anti-RANKL antibody is denosumab.

* * * * *

SEQUENCE LISTING

```
<160> NUMBER OF SEQ ID NOS: 21

<210> SEQ ID NO 1
<211> LENGTH: 21
<212> TYPE: DNA
<213> ORGANISM: Artificial Sequence
<220> FEATURE:
<223> OTHER INFORMATION: Primer

<400> SEQUENCE: 1
gctcatagct cttctccagg g                                             21

<210> SEQ ID NO 2
<211> LENGTH: 21
<212> TYPE: DNA
<213> ORGANISM: Artificial Sequence
<220> FEATURE:
<223> OTHER INFORMATION: Primer

<400> SEQUENCE: 2
cctgaaccct aaggccaacc g                                             21

<210> SEQ ID NO 3
<211> LENGTH: 18
<212> TYPE: DNA
<213> ORGANISM: Artificial Sequence
<220> FEATURE:
<223> OTHER INFORMATION: Primer

<400> SEQUENCE: 3
ctgaggccca gccatttg                                                 18

<210> SEQ ID NO 4
<211> LENGTH: 28
<212> TYPE: DNA
<213> ORGANISM: Artificial Sequence
```

```
<220> FEATURE:
<223> OTHER INFORMATION: Primer

<400> SEQUENCE: 4
gttgcttaac gtcatgttag agatcttg                                      28

<210> SEQ ID NO 5
<211> LENGTH: 20
<212> TYPE: DNA
<213> ORGANISM: Artificial Sequence
<220> FEATURE:
<223> OTHER INFORMATION: Primer

<400> SEQUENCE: 5
cttggacacc tggaatgaag                                               20

<210> SEQ ID NO 6
<211> LENGTH: 20
<212> TYPE: DNA
<213> ORGANISM: Artificial Sequence
<220> FEATURE:
<223> OTHER INFORMATION: Primer

<400> SEQUENCE: 6
cagcactcgc agtctgagtt                                               20

<210> SEQ ID NO 7
<211> LENGTH: 21
<212> TYPE: DNA
<213> ORGANISM: Artificial Sequence
<220> FEATURE:
<223> OTHER INFORMATION: Primer

<400> SEQUENCE: 7
ctgtgcgccc tccgtatctt a                                             21

<210> SEQ ID NO 8
<211> LENGTH: 21
<212> TYPE: DNA
<213> ORGANISM: Artificial Sequence
<220> FEATURE:
<223> OTHER INFORMATION: Primer

<400> SEQUENCE: 8
ggcggccagg ttccacttga g                                             21

<210> SEQ ID NO 9
<211> LENGTH: 19
<212> TYPE: DNA
<213> ORGANISM: Artificial Sequence
<220> FEATURE:
<223> OTHER INFORMATION: Primer

<400> SEQUENCE: 9
gtggccttgt cgctgtctt                                                19

<210> SEQ ID NO 10
<211> LENGTH: 23
<212> TYPE: DNA
<213> ORGANISM: Artificial Sequence
<220> FEATURE:
<223> OTHER INFORMATION: Primer

<400> SEQUENCE: 10
gcgcttggag tgatagaaat ctg                                           23
```

<210> SEQ ID NO 11
<211> LENGTH: 22
<212> TYPE: DNA
<213> ORGANISM: Artificial Sequence
<220> FEATURE:
<223> OTHER INFORMATION: Primer

<400> SEQUENCE: 11
gcgccgggcc agccgagact ac                                              22

<210> SEQ ID NO 12
<211> LENGTH: 22
<212> TYPE: DNA
<213> ORGANISM: Artificial Sequence
<220> FEATURE:
<223> OTHER INFORMATION: Primer

<400> SEQUENCE: 12
gtcccacacg agggtccgct gc                                              22

<210> SEQ ID NO 13
<211> LENGTH: 19
<212> TYPE: DNA
<213> ORGANISM: Artificial Sequence
<220> FEATURE:
<223> OTHER INFORMATION: Primer

<400> SEQUENCE: 13
tgcgcactcc ggcgtcccg                                                  19

<210> SEQ ID NO 14
<211> LENGTH: 25
<212> TYPE: DNA
<213> ORGANISM: Artificial Sequence
<220> FEATURE:
<223> OTHER INFORMATION: Primer

<400> SEQUENCE: 14
ccgagactac ggcggatcct aacag                                           25

<210> SEQ ID NO 15
<211> LENGTH: 30
<212> TYPE: DNA
<213> ORGANISM: Artificial Sequence
<220> FEATURE:
<223> OTHER INFORMATION: Primer

<400> SEQUENCE: 15
tcagtctatg tcctgaactt tgaaagcccc                                      30

<210> SEQ ID NO 16
<211> LENGTH: 23
<212> TYPE: DNA
<213> ORGANISM: Artificial Sequence
<220> FEATURE:
<223> OTHER INFORMATION: Primer

<400> SEQUENCE: 16
ccgcctgatg ccctccgctg tat                                             23

<210> SEQ ID NO 17
<211> LENGTH: 23
<212> TYPE: DNA
<213> ORGANISM: Artificial Sequence
<220> FEATURE:
<223> OTHER INFORMATION: Primer

```
<400> SEQUENCE: 17
cgggcccact cctcctcctc cac                                           23

<210> SEQ ID NO 18
<211> LENGTH: 20
<212> TYPE: DNA
<213> ORGANISM: Artificial Sequence
<220> FEATURE:
<223> OTHER INFORMATION: Primer

<400> SEQUENCE: 18
actttgtctc caatcctccg                                               20

<210> SEQ ID NO 19
<211> LENGTH: 20
<212> TYPE: DNA
<213> ORGANISM: Artificial Sequence
<220> FEATURE:
<223> OTHER INFORMATION: Primer

<400> SEQUENCE: 19
gtgcaccgga cataactgtg                                               20

<210> SEQ ID NO 20
<211> LENGTH: 20
<212> TYPE: DNA
<213> ORGANISM: Artificial Sequence
<220> FEATURE:
<223> OTHER INFORMATION: Primer

<400> SEQUENCE: 20
gttgaactcg tctccgatcc                                               20

<210> SEQ ID NO 21
<211> LENGTH: 20
<212> TYPE: DNA
<213> ORGANISM: Artificial Sequence
<220> FEATURE:
<223> OTHER INFORMATION: Primer

<400> SEQUENCE: 21
gcccctacct ccctacagac                                               20
```